(12) United States Patent
Abahri

(10) Patent No.: US 8,332,162 B2
(45) Date of Patent: Dec. 11, 2012

(54) APPARATUS AND METHOD FOR MEASURING THE PROPERTIES OF PETROLEUM FRACTIONS AND PURE HYDROCARBON LIQUIDS BY LIGHT REFRACTION

(75) Inventor: Tareq Abduljahl Abahri, Jaber Al-Ali (KW)

(73) Assignee: Kuwait University, Safat (KW)

( * ) Notice: Subject to any disclaimer, the term of this patent is extended or adjusted under 35 U.S.C. 154(b) by 0 days.

(21) Appl. No.: 13/366,257

(22) Filed: Feb. 3, 2012

(65) Prior Publication Data

US 2012/0143517 A1    Jun. 7, 2012

Related U.S. Application Data

(62) Division of application No. 12/475,571, filed on May 31, 2009, now abandoned.

(51) Int. Cl.
*G01N 31/08* (2006.01)
(52) U.S. Cl. .......................................................... 702/30
(58) Field of Classification Search ...................... 702/30
See application file for complete search history.

(56) References Cited

U.S. PATENT DOCUMENTS

2003/0193662 A1* 10/2003 DiFoggio et al. ............. 356/128
2004/0109156 A1*  6/2004 DiFoggio et al. ............. 356/128

* cited by examiner

*Primary Examiner* — Cindy H Khuu
*Assistant Examiner* — Manuel Rivera Vargas
(74) *Attorney, Agent, or Firm* — Richard C. Litman

(57) ABSTRACT

A Method and apparatus to accurately measure and display various properties of hydrocarbons and petroleum factions for a small volume of sample in a short period of time in one test with less cost and energy for the analysis by the method of light refection. The refraction of light through the sample is measured and compared to the refraction f the light through vacuum by the apparatus. The method of the invention comprises a property estimation from the apparatus to output a property estimate value. The property estimation means is equipped with a property estimation model for evaluating the property estimate value outputted from the property estimation model. The method is incorporated into standard or otherwise any refractive index test apparatus or refractometer to provide accurate measure of the thermodynamic and transport properties of pure hydrocarbons and undefined multi-component mixtures such as petroleum factions.

14 Claims, 17 Drawing Sheets

10

20

30

APPARATUS AND METHOD FOR MEASURING THE PROPERTIES OF PETROLEUM FRACTIONS AND PURE HYDROCARBON LIQUIDS BY LIGHT REFRACTION

CROSS-REFERENCE TO RELATED APPLICATION

This application is a division of U.S. patent application Ser. No. 12/475,571 filed May 31, 2009, now abandoned.

FIELD OF THE INVENTION

The present invention relates to material analysis and, in particular, the measuring method for rapidly predicting the thermophysical property values of pure and complex hydrocarbon mixtures by refractive index and its apparatus.

BACKGROUND OF THE INVENTION

Refractive index (n), also known as the index of Refraction, is defined as the ratio of the speed of light in a vacuum to the speed of light in a material and is dimensionless quantity shown by n:

$n$=velocity of light in the vacuum/velocity of light in the substance.

In other words, when a light beam passes form one substance (air) to another (a liquid), it is bent or refracted because of the difference in speed between the two substances. The refraction index indicates the degree of this refraction. Additional, refractive index is measures as the sine of the angle of bending (deflection) of light as it passes from one medium to another.

Refractive index is a property of optical materials that determines how fast light travels through it. The numerical n value indicates the light bending power of a medium such as a chemical. The greater the bending power, the greater the refractive index. In a medium, the speed of light depends on the wavelength and temperature. For this reason refractive index is usually measured and reported at 20° C. with the D line sodium light.

The refractive index is a thermodynamic property and is a state function, which for a pure fluid depends on temperature and pressure. Since the velocity of light in a fluid is less than the velocity of light in a vacuum, its value of a fluid is greater than unity. Liquids have higher values of refractive index than that of gases. For gases the values of refractive index are very close to unity. The refractive index or refractivity (n) can be easily measured by the sodium D line of a simple refractometer at a temperature of interest. Values of n at 20 and 25° C. are given by the API Technical Data Book for many different hydrocarbons.

All frequencies of electromagnet radiation (light) travel in the same speed in vacuum ($2.998 \times 10^8$ m/s); however, in a substance the velocity of light depends on the nature of the substance (molecular structure) as well as the frequency of the light. For this reason, standard values of refractive index must be measured at a standard frequency. Usually the refractive index of hydrocarbons is measured by the sodium D line at 20° C. and 1 atm. In some references the values of refractive index are reported at 25° C.; however, the refractive index is usually measured at 20° C. and 1 atm, and is usually used as a characterization paramount for hydrocarbons and petroleum factions.

Refractive index testing procedure is used to determine the quality of every essential oil. Light behaves differently depending upon the density of the material it is passing through. The reading is compared to established literature; deviations are indicative of adulteration. The index of air is 1.00 and all indices are referred to the index of air, i.e. the index of water being 1.33 means that the speed of light in air is 1.33 times greater as the speed of light in water. Ice refractive index of 1.31, while air has a refractive index of 1.000277. Refractive indexes of hydrocarbons vary from 1.3 for propane to 1.6 for some aromatics; however, aromatics have refractive index value greater than napthenes, which in turn have refractive indexes greater than paraffins.

Refractive index (n) is a useful parameter to characterize hydrocarbon systems and is needed to estimate the composition of undefined petroleum factions. For example, the refractive index at some reference conditions (i.e., 20° C. and 1 atm) is a useful characterization parameter to estimate the composition and quality of petroleum factions. It is also used to estimate many physical properties such as molecular weight, equation of state paraments, the critical constants, or transport properties of hydrocarbon systems.

For pure liquids and mixtures, refractive index is a bulk property that can be easily and accurately measured by an optical instrument called refractometer. Certain types of refractometers can be used for measuring gases, liquids, and even transparent or translucent solids such as gemstones.

Refractive index can be measured by digital refractometers with a precision of 0.0001 and temperature precision of 0.1° C. The amount of sample required to measure refractive index is very small and ASTM D1218 provides a test method for clear hydrocarbons with values of reflective indexes in the range of 1.33-1.5 and the temperature range of 20-30° C. In the ASTM D1218 test method the Baush and Lomb refractometers is used. Refractive index of viscous oils with values up to 1.6 can be measured by the ASTM D1747 test method. Samples must have clear color to measure their refractive index; however, for darker and more viscous sample in which actual refractive vale is outside the range of application of refractometer, samples can be diluted by a light solvent and refractive index of the solutions should be measured. From the composition of the solution and refractive index of pure solvent and that or the solution, refractive index of viscous samples can be determined. A model Abbe refractometer (Leica), for example, measure refractive index of liquids within the temperature range of −20 to 100° C. with temperature accuracy of ±0.01° C. Because of simplicity and importance of refractive index it would be extremely useful if laboratories measure and report its value at 20° C. for a petroleum product, especially if the composition of the mixture is not reported.

There are four main types of fluid refractometers: traditional handheld refractometers, digital handheld refractometers, Abbe refractometers, and inline process refractometers.

Ad traditional handheld refractometer is a handheld analog instrument for measuring refractive index that works on the critical angle principle. They utilize lenses and prism to project a shadow line onto a small glass reticule inside the instrument, which is then viewed by the user though a magnifying eyepiece. N use, a sample is sandwiched between a measuring prism and a small cover plate. Light traveling through the sample is either passed through to the reticule or totally internally reflected. The net effect is that a shadow line is formed between the illuminated area and the dark area. It is at the point that this shadow line crosses the scale that a reading is taken. Because refractive index is very temperature dependent, it is important to use a refractometer with automatic temperature compensation. Compensation is accomplished through the use of a sample bi-metal strip that moves a lens or prism in response to temperature changes.

In optics, a digital handheld refractometer is an instrument for measuring the refractive index of materials. Most operate on the same general critical angel principle as a traditional handheld refractometer. The difference is that light for an LESD light sources is focused on the underside or prism element. When a liquid sample is applied to the measuring surface of the prism, some of the light is transmitted through the solution and lost; while the remaining light is reflected onto a linear array of photodiodes creating a shadow line. The refractive index is directly related to the position of the shadow line on the photodiodes. The more elements there are in the photodiode array, the more precise the readings will be, and the easier it will be to obtain readings for emulsions and other difficult-to-read fluids that from fuzzy shadow lines. Once the position of the shadow line has been automatically determined by the instrument, the internal software will correlate the position to refractive index, or to another unite of measure related to refractive index, and display a digital readout on an LCD or LED scale.

Digital handheld refractometers are generally more precise than traditional handheld refractometers, but less precise than most benchtop refractometers. Then also may require a slightly larger amount of sample to read from (since the sample is not spread thinly against the prism. Nearly all digital refractometers feature automatic temperature compensation (for Brix at least). Like most forms of electronics, this type of unit is always getting smaller and more ergonomic.

Am Abbe or laboratory refractometer is a bench-top refractometer that offers the highest precision of the different types of refractometers. Nearly one and a half century after their introduction, refractometers have come a long way in terms of usefulness, though their principle of operation has changed very little.

Ernst Abbe, working for the Zeiss Company in Jena, Germany in the late 1800s, was the first to develop a laboratory refractometer. These first instruments had built-in thermometers and required circulating water to control instrument and fluid temperatures. They also had adjustments for eliminating the effect of dispersions. These first instruments had analog scales from which the readings were taken.

There have been many refinements regarding teas of use and precision to these instruments over the decades, but they still operate on the same principle. They are still used today as an inexpensive alternative to digital laboratory refractometers. They are also possibly the easiest method to find the refractive index of solid samples, such as glass, plastics, and polymer films. Some Abbe refractometers utilize a digital display for the measurement, to eliminate the need for discerning between small graduations. The user still has to adjust the view to obtain the reading, however.

The first truly digital laboratory refractometers began appearing in the late 197s and early 19802, and no longer depended on the user's eye to determine the reading. They still required the use of circulating water baths to control instrument and fluid temperature. They did, however, have the ability to electronically compensate for the temperature differences of many laboratory refractometers, while much more accurate and versatile than thief analog Abbe counterparts, are not capable of reading solid samples.

IN the late 1990s, Abbe refractometers with the capability to read at wavelengths other than the standard 589 nanometers became availability. These instruments utilize special filters of the desired wavelength of light, well into the near infrared (though a special viewer is required to see the infrared rays). Multi-wavelength Abbe refractometers can be used to very easily determine a sample's Abbe number.

The most advanced instruments of today use solid-state Peltier effect devices to heat and cool the instrument and the sample, eliminating the dependence on an external water bath. The software on most of the current instruments is now very advanced and offers features such as programmable user-defined scales and a history function that recalls the last several measurements. Several manufacturers provide easily usable controls, with the capability to operate from and export readings to a linked computer.

Previously refractive index readings from manual refractometers were obtained by visual inspection. A sample is placed in the refractometer and a knob that moved a graduated scale is rotated until two lines representing light refection through the material and space or air are aligned then the meter reading is recorded using visual inspection. Currently lab-scale automatic refractometers are being used which output the numeral value of the refractive index using a digital display.

Inline process refractometers are a type of refractometer designed for the continuous measurement of a fluid flowing through a pipe or inside a tank throughout the manufacturing process. These refractometers typically consist of a sensor, placed inline with the fluid flow, couple to a control box. The control box usually provides a digital readout as well as 4-20 mA analog outputs and relay outputs for controlling pumps and valves.

Refractometers are widely used in oil industry, fat industry, pharmaceutical factories, paint, and food processing, among others. A refractometer can be used to determine the identity of a n unknown substance based on its refractive index, to assess the purity of a particular substance, or to determine the concentration of one substance dissolved in another. Most commonly, refractometers are used for measuring fluid concentrations such as the sugar content ((brix level) of fruits, vegetables, juices and carbonated beverages, or of cutting fluids, urine specific gravity, blood protein concentration, salinity, antifreeze, industrial fluids, etc. Materials measured can be chemicals, syrups, Uren, food, pharmaceuticals petroleum products and the like. For testing refractive index, honey, coolants, specific gravity in urine, etc. Measure soluble solids (BRIX) percentage in fruit, juices, cooking oils and other various solutions. What current refractometers cant do is directly measure and display the thermophysical properties of the material being tested.

Prior Art Reference and Discussion

Various methods are known for the evaluation of fluid properties indirectly. Conventional gas and liquid chromatography (GLC), infrared and mass spectroscopy (IR), Nuclear magnetic resonance (NMR), hydrogen ion nuclear magnetic resonance (HNMR), nitrogen nuclear magnetic resonance (NNMR), and Fourier Transform Infrared Spectroscopy (FTIR) techniques and the like enable sampling and evaluation of a fuel's components but the equipment is both expensive and ordinarily not available for evaluation of a delivered product. It would therefore be highly desirable to have a method for rapidly measuring the properties of pure hydrocarbons and hydrocarbon mixtures using a single apparatus, and preferably an apparatus that is so simple and widely used in the industry such as the refractometer apparatus for example.

Gas chromatography has been used to predict petroleum properties in gasoline-type petroleum products through indirect measurements. Crawford and Hellmuth, Fuel, 1990, 69, 443-447, describe a chromatographic analysis that is able to predict the octane number of various effluents that come from the refinery, by application of mathematical models that are based on the statistical technique of principles component regression (PCR).

Japan Patent n. JP3100463 (1991) to TAKAMURA et al. discloses a method and instrument for measuring cetane value or cetane index in a sample from an extremely small volume of sample oil in a short period of time by separating and eluting the respective components contained in the sample to be measured by using gas chromatograph couple to mass spectrometer. The cetane value or cetane index is determined by substituting the variables with the regression formula in which parameters are previously determined.

Japan Patent n. JP9318613 (1997) to Sasnano discloses a measuring method of research octane number of gasoline by gas chromomatograph and its apparatus, by separating components of a gasoline sample with a gas chromatograph using a specific column, and by substituting a specific equation with a physical property of a component which is selected by being only identified on a peak area value equal to or more than a predetermined value.

U.S. Pat. No. 5,699,269 (1997) to Ashe, et al. discloses a method for predicting chemical or physical properties of crude oils or their boiling factions which comprise CG/MS analysis wherein the often collinear data generated is treated by multivariate correlation methods.

U.S. Pat. No. 6,275,775 (2001) to Baco, et al. discloses a method for determining at least one physico-chemical property of a petroleum fraction by gas chromatography couple with an atomic emission detector (GC-AED) to determine the distribution of an element from the group of carbon, hydrogen, sulfur, and nitrogen, as a function of the boiling points of the components of the sample, and the coefficients of the correlative model are determined from all of the data. The petroleum fraction whose property is to be determined is analyzed by chromatography under the same conditions, and the data that obtained are multiplied by the coefficients for the model to determine the value of said property as a function of the boiling pointes of its components. Application to the determination of the cetane number as a function the distillation profile of the components of the petroleum faction.

Near infrared spectrometric analysis has been used to determine indirectly the qualitative properties of various hydrocarbon samples. Examples are": "Prediction of Gasoline Octane Number from Near Infrared Spectral Features in the Range 660-1215 nm" by Jeffery J. Kelly, et. Al., Analytical Chemistry, Volume 61, Number 4, Feb. 15, 1989, pp. 31320, and "Predicting Gasoline Properties Using Near-IF spectroscopy" by Stephen J. Swarin and Charles A. Drumm, Spectroscopy, Volume 7, number 7, September 1992, both described a method of predicting the antiknock index of gasoline using near infrared spectrometry. These methods described passing energy in the near infrared region of the electromagnetic spectrum through a sample of gasoline absorption at each wavelength. This measurement results in a spectral profile, or spectrum, which can then be compared to the spectrum of a data set of samples having know antiknock indexes.

U.S. Pat. No. 4,800,279 (1889) to Heiftje, et al. discloses methods and devices for near-infrared evaluation of physical properties of samples. Methods are disclosed for quantifying physical properties of gaseous, liquid or solid samples.

One method of evaluating fuel properties is known as near-IR spectroscopy, in which a sample is excited with light from a near-IR light source. Since known fuel components exhibit characteristic vibrational mode overtones when excited in the near-IF, the vibrations of unknown constituents can be evaluated and classified accordingly. The typical evaluative process is complex, involving substantial non-linear data comparisons. Kelly, et al, describe such a method in "Prediction of Gasoline Octane Numbers from Near-Infrared Spectal Features in the Range 660-1215 nm, "Vol. 61, Analytical Chemistry, No. 4, p 313, Feb. 15, 1989, in which vibrational overtones and combination banks of CH groups of methyl, methylene, aromatic, and olefinic functions were observed in near-IF spectral region. With the ai of multivariate statistical analysis, the spectral features were correlated to various fuel quality parameters, include octane number. The property or yield is usually determined by applying a correlation between the priority or yield and the absorbance values. The correlation is determined experimentally by multivariate regression or neural network and is dependent upon the type of spectrometer employed, the property or yield to be determined, and the frequencies used.

U.S. Pat. No. 4,963,745 (1990) to Magard discloses an octane measuring process and device comprising the near infrared absorbance of the methyne band measures octane (pump, RON, and MON) with excellent correlation and can be used for gasoline blending. This patent is an example of near infrared absorbance evaluation between 1200 and 1236 nm applied to the methyne bank along with the tertiary butyl band, indicative of sources of free radicals which seem to lead to smooth combustion. The signal processing techniques used, however, are complex, including first, second, third, and fourth or higher derivative processing as well as various known curve fitting techniques.

U.S. Pat. No. 5,362,965 (1994) to Maggard discloses an indirect method for determining oxygenate content and/or octane of hydrocarbon fuels using near-infrared absorption spectra selecting nanometer frequencies in the range 1,300 to 1,359 to reduces the temperature dependence of calibration equations that predict values representative of both oxygenate content and octane.

U.S. Pat. Nos. 5,349,188 and 5,349,189 both issued (1994) to Maggard discloses a process and apparatus for analysis of hydrocarbons by near-infrared spectroscopy to measure the weight percent, volume percent, or even mole percent of each component, e.g. PIANO (paraffin, isoparaffin, aromoatic, napthens, and olefins), octane (preferably research, motor or pump), and percent of various hydrocarbons, e.g. alpha olefins.

U.S. Pat. No. 5,121,785 (1992) to Maggard et al. discloses determination of aromatics in hydrocarbons by near infrared spectroscopy of mid-distillate hydrocarbon fuels.

Preferred NIR bands of 1650-1700 and 2120-2256 exhibit excellent correlation with aromatics content.

U.S. Pat. No. 5,121,377 to Brown discloses a method for correcting spectral data for dat due to the spectral measurement process itself and estimating unknown property and/or composition data of a sample using such method. The correction method is preferably included in a method of estimating unknown property and/or composition data of a sample under consideration.

U.S. Pat. No. 5,446,681 (1995) to Gethner, et al. discloses a method of estimating property and/or composition data of a test sample. A method of operating a spectrometer to determine property and/or composition data of a sample compares an on-line spectral measurement of the sample using a computer controlled spectrometer, statistical analysis of the sample data based upon a statistical model using sample calibration data, and automatically identifying a sample if necessary based upon statistical and expert system (rule-based) criteria.

U.S. Pat. No. 5,424,959 (1995) to Reyes, et al. discloses a method for interpretation of fluorescence fingerprints of crude oils and other hydrocarbon mixtures using neural networks. The artificial intelligence system is used with a conglomeration of fluorescence data to provide a method of improving recognition of an unknown from its spectral pattern.

U.S. Pat. No. 5,218,529 (1993) to Meyer, et al. discloses a neural network system and methods for analysis of organic materials and structures using spectral data. Characteristic spectra are obtained for the materials via spectroscopy techniques including nuclear magnetic resonance spectroscopy, infrared absorption analysis, x-ray analysis, mass spectroscopy and gas chromatography.

Japan Patent no. JP9243634 (1997) to Sato and Fujimoto discloses an apparatus for estimating properties for petroleum product. The property estimation means is equipped with a property estimation model using a neutral network and a property analyzed value obtained by analyzing the petroleum product. In the property estimation model, properties can be calculated from operation data within a real time.

U.S. Pat. No. 5,452,232 (1995) to Espinosa, et al. discloses a method and apparatus for determining a property or yield of a hydrocarbon product based on Near Infra-Red (NIR) spectrum of the feedstock.

U.S. Pat. No. 5,360,972 (1994) to DiFogglo, et al. discloses a method for improving chemometric estimations of the physical properties of materials. The invention discloses a method for improving the estimation of physical properties of a material based on the near and mid-infrared spectrum of the material. The method further discloses use of a combination of Raman spectroscopy, gas chromatography, and mid-infrared spectroscopy for the same purpose of the invention.

U.S. Pat. No. 5,225,679 (1003) to Clarke, et al. discloses methods and apparatus for determining hydrocarbon fuel properties. Detection is made of absorption related to signature vibrational modes associated with the fuel component molecules when excited in the mid-IR. From the determined fuel component quantity and know characteristics, the fuel solution properties are predicted. In one embodiment, octane rating and vapor pressure for a fuel solution is determined in-situ and in real time.

U.S. Pat. No. 5,412,581 (1995) to Tackett discloses method for measuring physical properties of hydrocarbons using near infrared spectrum measurements.

In all the above patents the property value for the petroleum hydrocarbon mixture was calculated, using a mathematical correlation or neural network the impute parameters of which are either the GC-measured pure component concentrations or the spectral parameters. Since a property like octane number for example can be estimated by fitting GC and IR characteristic output data then the same can be done for all thero-physical properties as well as using the characteristic output date from light refraction.

All the above patents disclose using either infrared or gas chromatography for the purpose of predicting one or more proprieties of pure hydrocarbons or petroleum fractions.

None of the above patents claims or discloses using refractive index or refractometry for that purpose. The method of the present invention meets the novelty requirement.

European paten no. EP0071143 (1083) to Partky, discloses a refractometer that measures the refractive index property but not the other thermophysical properties. World Paten no. WO9509356 (19995) to Lawrence et al. and U.S. Pat. No. 5,482,076 (1995) to Schopper, et al. both disclose a fluid detection system based on the index of refraction which does not provide the fluid thermophysical properties.

SUMMARY OF THE INVENTION

This invention relates to a method for predicting physical, performance, perceptual and/or chemical properties of pure hydrocarbons and hydrocarbon mixtures. The analytical method is able to predict a set of date that consist of global petroleum properties of pure hydrocarbons and hydrocarbon mixtures, form correlative mathematical models which will be determined, according to conventional analytical methods, ie. The refractive index.

It is a purpose of this invention to calculate the properties of a hydrocarbon sample with high reliability. The method of the invention comprises a property estimation apparatus has a property estimation means estimating the properties of a hydrocarbon product from the apparatus to output a property estimate value. The property estimation means is equipped with a property estimation model for a evaluating the property estimate value outputted from the property estimation model and a property analyzed value obtained by analyzing the hydrocarbon sample. The property estimation model may comprise at least a regression algorithm, a neural network algorithm, an optimization algorithm, or generic algorithm, or the like.

In this invention a mathematical algorithm is used with refractive index data to provide a method of improving recognition of an unknown from its refractive as shown in FIG. 1. Customized mathematical algorithms allow the ultimate organization and resourceful use of assumption-free variables already existing in refractive index apparatus for a much more comprehensive, discrete and accurate differentiation and matching of thermo-physical and transport properties than is possible with human memory. The invention provides increased speed of fingerprinting analysis, accuracy and reliability together with a decreased time, cost and energy for the analysis.

The present invention is based on the recognition that the molecules of components of a hydrocarbon solution each exhibit physical and chemical characteristics that such signatures are exhibited in terms of the refractive index and that such physical and chemical characteristics can be correlated either linearly or nonlinearly with said index of the solution.

Accordingly, in one embodiment of the invention, a know volume of a hydrocarbon sample, placed in a refractometer and the refractive index reading is recorded. The refractive index is indicative of the characteristics of the hydrocarbon of interest. The refractive index and that such physical and chemical characteristics can be correlated either linearly or nonlinearly with said index of the solution.

In another preferred embodiment the refractive index data is plausibly correlated to the property of the hydrocarbon using optimization algorithms. In another preferred embodiment the refractive index data is correlated to the property of the hydrocarbon using simple regression techniques. Yet in another preferred embodiment the refractive index data is correlated to the property of the hydrocarbon using neural networks.

In a preferred embodiment, the refractive index data is used to compute the composition and the properties of the hydrocarbon sample in the processing section within the refractive index, apparatus, and a display output is then generated accordingly. In another embodiment the refractive index data from the refractive index apparatus is processed in a processing section out of the device and a display output is then generated accordingly. Likewise, other components and properties may be found and quantified in a similar manner.

The refractive index method described above can be used to predict a wide range of chemical and physical properties (including performance and perceptual properties) of petroleum fuels such as, API gravity @ 15° C., Specific Gravity, Density @ 20° C., Average Boiling Point, Watson characterization factor, Molecular Weight, Critical Volume, Reid Vapor Pressure, Kinematic viscosity @ 37.8 & 98.9° C., True critical temperature, Pseudocritical temperature, True critical pressure, Pseudocritical pressure, Acentric factor, Net heat of combustion @ 25° C., conductivity @ 25° C., Research octane number, Motor octane numbers, Heat of Vaporization at the Normal Boiling point, Carbon to hydrogen content, True vapor pressure, Flash point Freezing point, Surface tension of liquid, Aniline point, Cloud point, Critical compressibility factor, and Compositional Analysis for sulfur, paraffin, naphthenes, and aromatics including mono-aromatics, polyaromatics, and the like, within the refractive index apparatus in a shot time period and using one test.

Best of such simplicity, the invention enables hydrocarbon properties to be easily determined and displayed. In fact, while the ASTM methods of obtaining the physico-chemical properties involved labor-intensive laboratory procedures, the present invention provides an equivalent property measurement in-situ and in real-time. The invention provides increased speed of fingerprinting analysis, accuracy and reliability together with a decreased learning curve and heighten objectivity for the analysis.

Such apparatus is particularly useful for recognizing and identifying organic compounds such as complex hydrocarbon, whose analysis conventionally require a high level of training and many hours of hard work to identify, and are frequently indistinguishable from one another by human interpretation. The present invention is therefore a valuable addition to the art of fuels properties detection.

Upon further study of the specification and appended claims, further objects and advantages of this invention will become apparent to those skilled in the art.

BRIEF DESCRIPTION OF THE DRAWINGS

The above and other aspects, features, methods, processes and advantages of the present invention will be better and more fully understood by those skilled in the art with reference to the following detailed and more particular description of specific and preferred embodiments thereof, presented in conjunction with the following drawings to show how the same may be carried into effect, wherein.

DETAILED DESCRIPTION OF THE INVENTION

Figure 1:
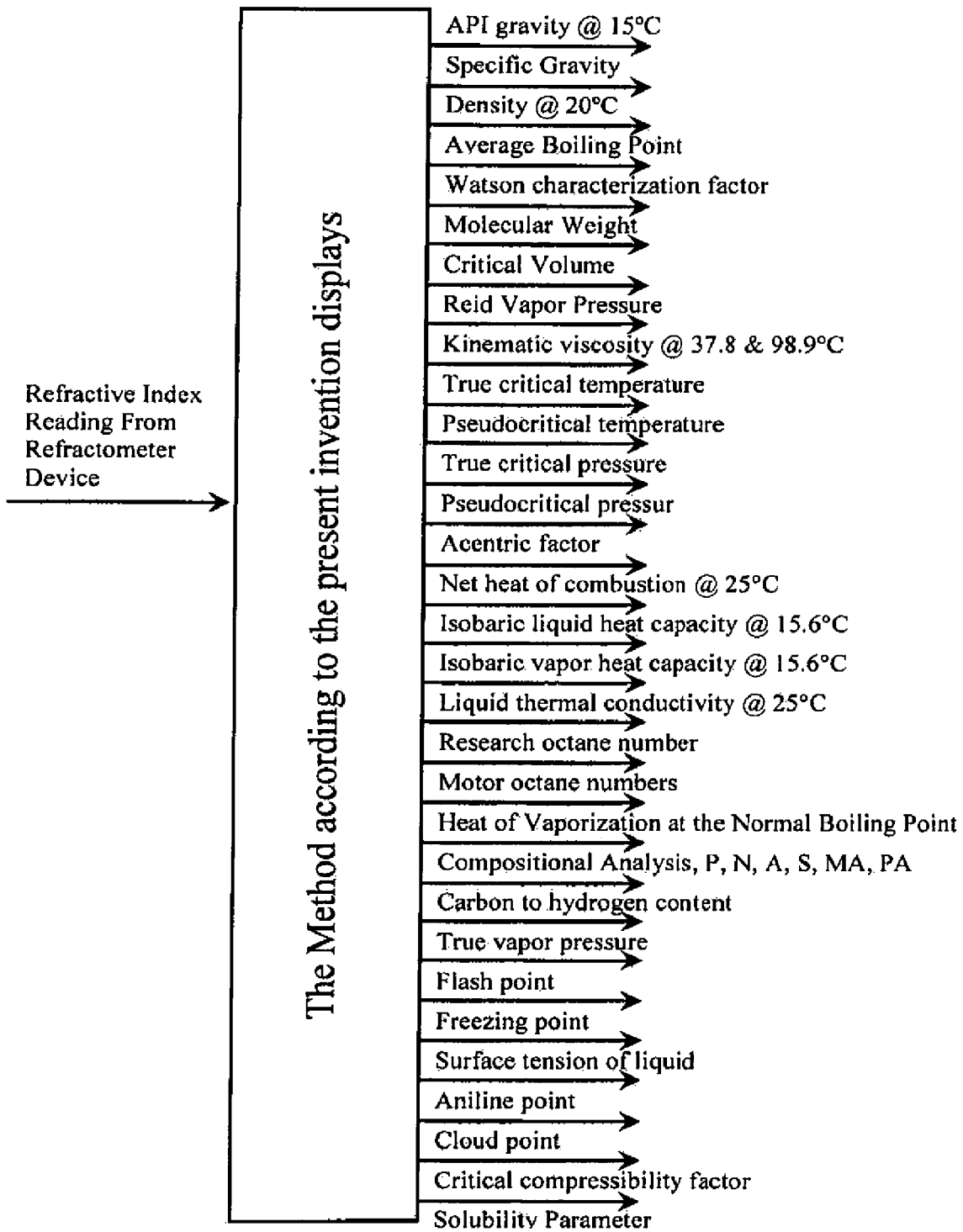
FIG. 1 is shows a simplified block diagram of the invention within its environment, wherein the measured properties of petroleum fractions are illustrated.

There will now be described, by way of example only, the best mode contemplated by the inventor for carrying out the invention. In the following description numerous specific details are set forth in order to provide a thorough understanding of the present invention. It will be apparent however, to one skilled in the art, that the present invention may be practiced without limitation to these specific details. In other instances, well known methods and structures have not been described in detail so as not to unnecessarily obscure the present invention.

It is therefore an object of the present invention to provide a simple method and apparatus for hydrocarbon property detection.

It is another object of the present invention to provide a relatively inexpensive, real-time insitu detection method and apparatus for detection of the properties of a pure hydrocarbon and a hydrocarbon solution.

It is still another object of the present invention to provide a simplified method and apparatus for obtaining refractive index data relating to a pure hydrocarbon or hydrocarbon solution and from which predicting fuel properties without complex analytical processing techniques.

It is further an object of the present invention to provide a method for predicting various properties of a pure hydrocarbon or hydrocarbon solution based on the knowledge of the mixture's refractive index that is easily measurable in the laboratory using refractometers Yet, its further an object of the present invention to is to provide a method to predict the various properties of a pure hydrocarbon or hydrocarbon solution based on the knowledge of the mixture's refractive index using refractometer which can be incorporated into the ASTM reflective index apparatus to predict and display the various prosperities for the petroleum faction using one single laboratory text and apparatus.

It is further an object of the present invention to provide a procedure for predicting the fluid properties that is simple and straightforward.

It is further an object of the present invention to provide a model that requires limited information form readily available lab analysis and simple analytical characterization to describe a petroleum feedstock.

It is further an object of the present invention to provide a method for inline prediction the global properties of pure hydrocarbon and hydrocarbon mixtures during various physical and chemical processing scenarios as they progress.

It is further an object of the present invention to provide a computerized procedure that can be incorporated as software in the ASTM refractive index apparatus hardware to provide measurement of the properties of pure components and of petroleum fractions using one single laboratory test.

It is further an object of the present invention to provide a method an apparatus that will leads to large savings in terms of energy, time and cost whereby one refractometer test can replace the test equipment needed to predict all of the properties of a hydrocarbon or a hydrocarbon mixture such as petroleum.

It is further an object of the present invention to provide a method that can calculate the properties of petroleum fractions with good accuracy when at least one bulk property (e.g. ASTM refractive index) is available.

It is further an object of the present invention to provide a method that is applicable to any petroleum faction or pure hydrocarbons.

The invention will now be explained with reference to some exemplary equations and n) correlations whereby further objects and advantages of this invention will become apparent to those skilled in the art.

Pure Hydrocarbon Liquids

The value of the refractive index outputted from the conventional digital refractometer incorporated (integrated) in this invention is used to calculate the API gravity using the following exponential expression, $$API = 5 \times 10^7 \exp(-9.5788n) \qquad (2)$$

Figure 4:
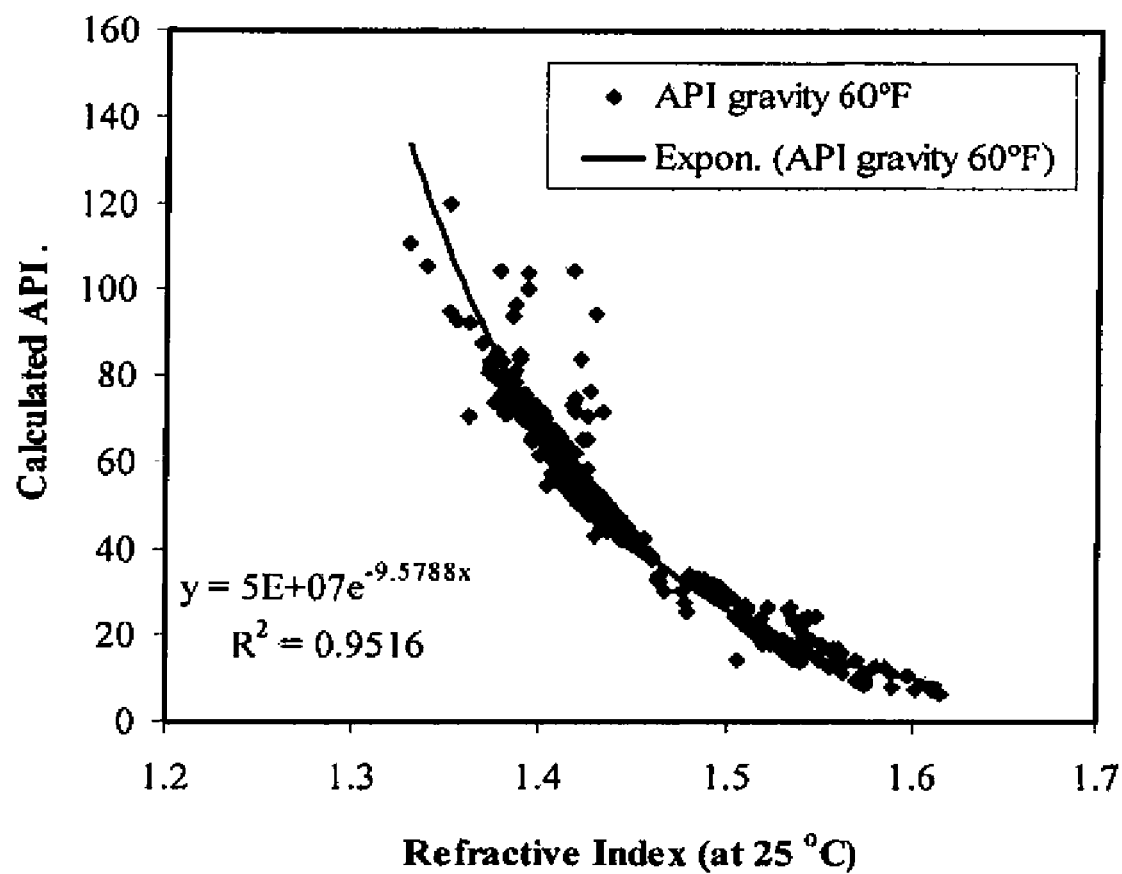
FIG. 4 shows the API gravity of 424 pure hydrocarbon liquids calculated using exponential expression and refractive index measured at 25 degrees centigrade, evaluated in practice of the invention.

This equation was developed using the experimental data for the API gravity of 424 pure hydrocarbon liquids and refractive index measured at 25 degrees centigrade. This equation applies for pure hydrocarbon liquids with minimum refractive index of 1.3294 and a maximum of 1.6151 which corresponds to a minimum API of 6 and maximum of 120. The question is applicable to different types of hydrocarbons like paraffins, iso-paraffins, olefins, naphthenes and aromatics. It has an average percentage error of 5 and a correlation coefficient of 0.95 as shown in FIG. 4.

The specific gravity SG at 15 degrees centigrade can be obtained from the following well know prior relation:

$$API = \frac{141.5}{SG} - 131.5 \qquad (3)$$

Which upon rearrangement becomes as follows, $$API = \frac{141.5}{API + 131.5} \qquad (4)$$

Numerical value of $d_{20}$ for a given compound is very close to the value of SG, which represents density at 15.5° C. in the unit of g/cm$^3$. The most convenient way to estimate $d^{20}$ is through specific gravity. As a rule of thumb $d_{20}$=0.995 SG. One can use this equation to obtain a value of density, $d_{20}$, at 20° C. (g/cm$^3$) from the specific gravity at 15.5° C. from the prior art relation by Riazi et al. as follows, $$d_{20} = SG - 4.5 \times 10^{-3}(2.34 - 1.9SG) \qquad (5)$$

Similarly, the value of the refractive index outputted from the conventional digital refractometer incorporated (integrated) in this invention is used to calculate the solubility parameter using the following linear expression, $$SP + 12.838n - 10.542 \qquad (6)$$

Figure 5:
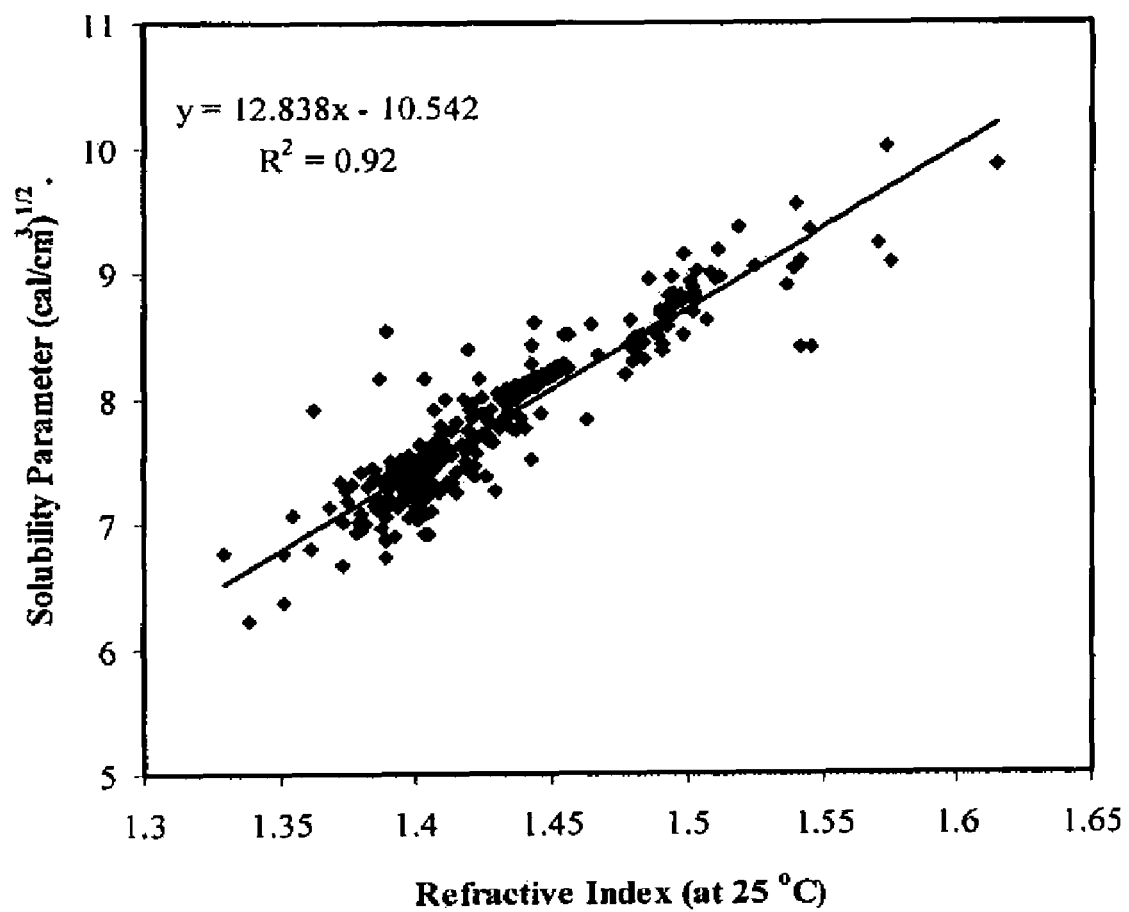
FIG. 5 shows the solubility parameter of 287 pure hydrocarbon liquids calculated using linear expression and refractive index measured at 25 degrees centigrade, evaluated in practice of the invention.
Figure 6:
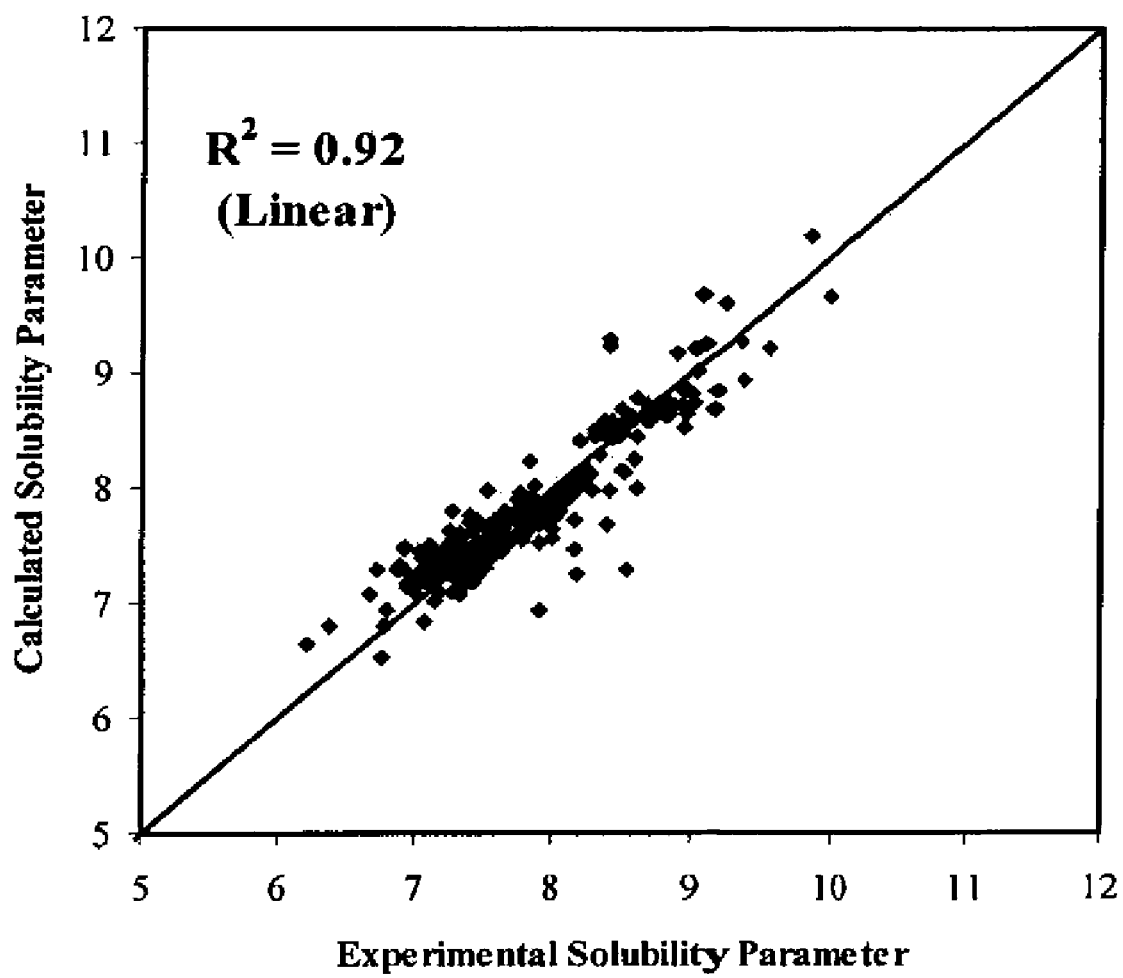
FIG. 6 shows the parity diagram for the solubility parameter or 287 pure hydrocarbon liquids calculated using linear expression and refractive index measured at 25 degrees centigrade, evaluated in practice of the invention.

This equation was developed using the experimental data for the solubility parameter of 287 pure hydrocarbon liquids and their refractive index measured as 25 degrees centigrade. This equation applies for pure hydrocarbon liquids with minimum refractive index of 1.3284 and a maximum of 1.6151 which corresponds to a minimum solubility parameter of 6.2 and maximum of 10 (cal/cm$^3$)$^{0.5}$. The equation is applicable to different types of hydrocarbons like paraffins, iso-paraffins, olefins, naphthenes, and aromatics. It has an average percentage error of 2.2% and a correlation coefficient of 0.92 as shown in FIG. 5. The parity diagram for the same is shown in FIG. 6.

Petroleum Fractions

The global properties are calculated for the petroleum fraction using well established methods in the literature or from methods developed specifically for this purpose. The determination of the petroleum fractions global properties involves either accessing standard correlations or simulating various thermodynamic experiments. Several charts and correlations in the literature predict the physical, thermodynamic, and transport properties of undefined mixtures, based on the boiling pint, specific gravity, and some characterization factors. Examples of such chars and correlations are available in the API-TDB [10] and other references. The global properties determined by the present invention as shown in FIG. 1.

The value of the refractive index outputted from the conventional digital refractometer incorporated (integrated) in this invention is used to calculate the API gravity using the following linear expression, $$API = -320.77n + 501.4 \qquad (7)$$

Figure 7:
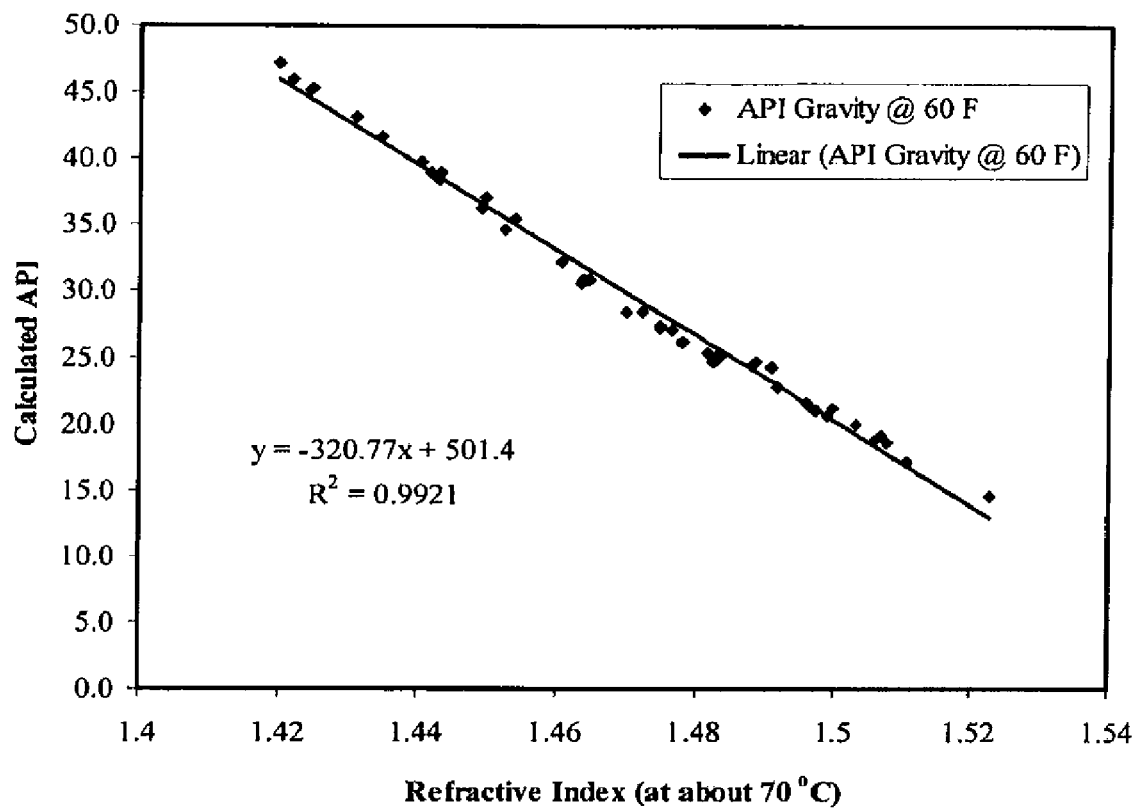
FIG. 7 shows the API gravity of 42 petroleum factions calculated using linear expression and refractive index measured at 50 to 70 degrees centigrade, evaluated in practice of the invention.
Figure 8:
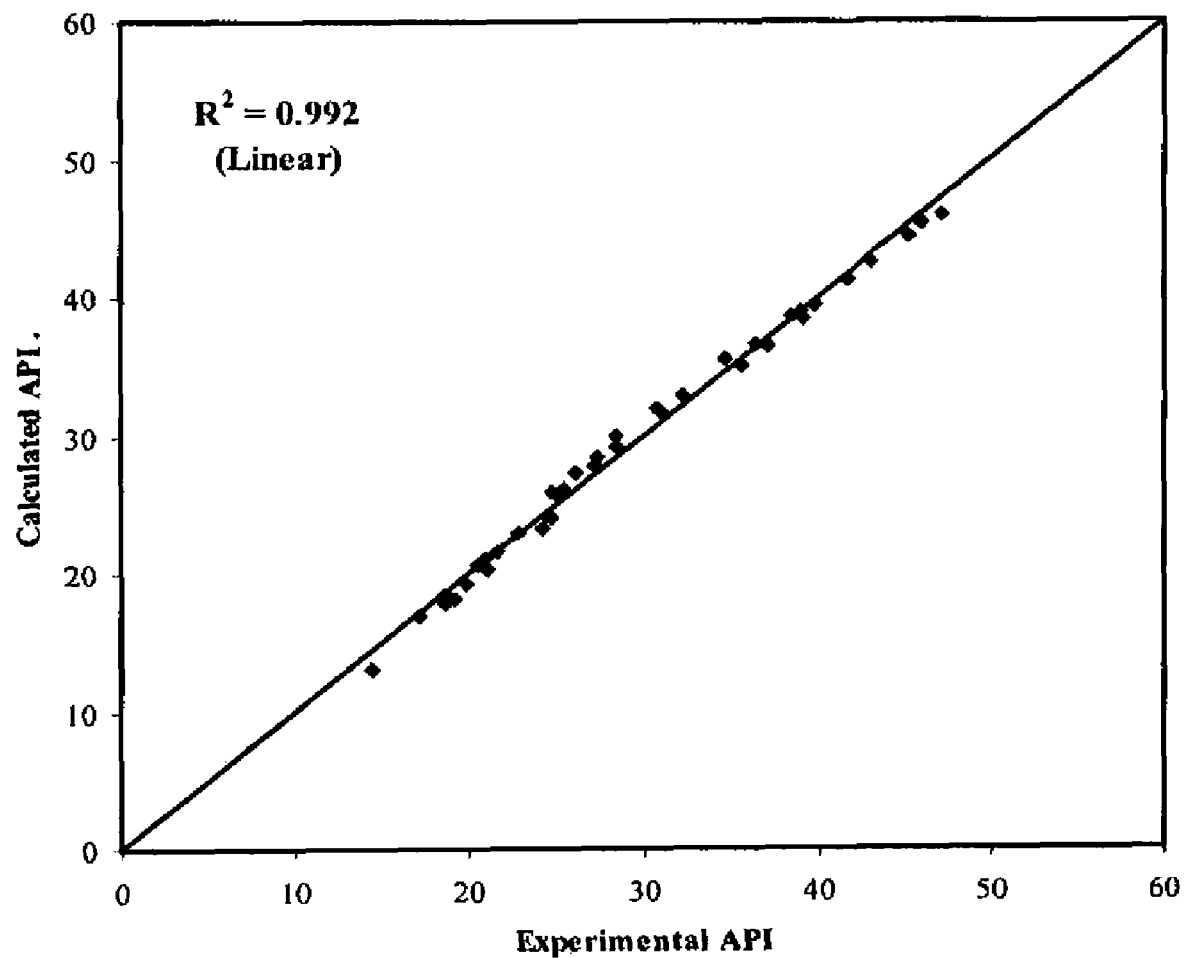
FIG. 8 shows the parity diagram for the API gravity of 42 petroleum factions calculated using linear expression and refractive index measure at 50 to 790 degrees centigrade, evaluate in practice of the invention.

This equation was developed using the experimental data for the API gravity of 42 petroleum fraction and refractive index measured at 53 to 70 degrees centigrade. This equation applies for petroleum fractions with minimum refractive index of 1.42 and a maximum of 1.5227 which corresponds to a minimum API of 14 and maximum of 47. The equation is applicable to different types of petroleum fraction like naphtha, kerosene, middle distillated, heavy distillate, vacuum distillate, gasoil, heavy gasiol, and cracked feed. It has an average percentage error of 2.5% and a correlation coefficient pf 0.992 as shown in FIG. 7. The parity diagram showing the accuracy of the predictions is shown in FIG. 8. Source of error in the calculated API related to different temperature values at which the refractive index is measured between 53 to 70 degrees C., but still the predictions are very accurate.

Alternatively the following quadratic expression may be used to obtain better predictions $$API = 836.17n^2 - 2775.4n + 2302.2 \quad (8)$$

Figure 9:
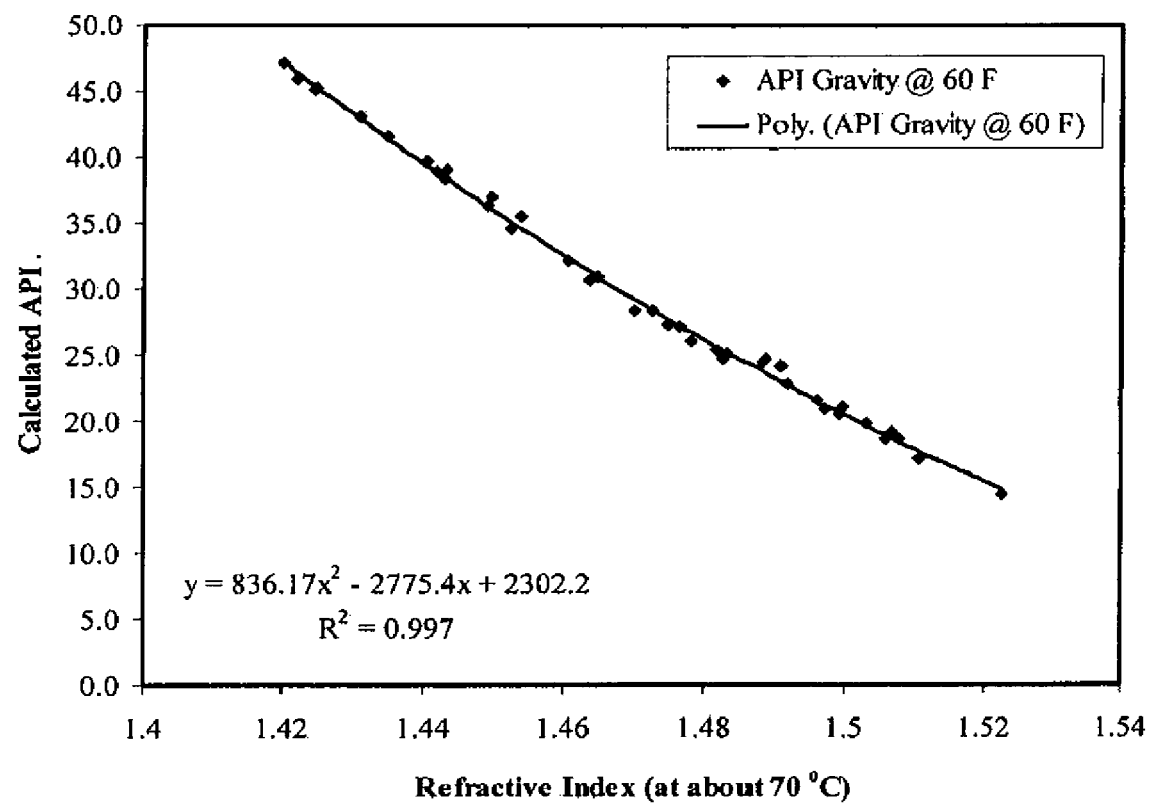
FIG. 9 shows the API gravity of 43 petroleum fractions collocated using quadratic expression and refractive index measured at 50 to 70 degrees centigrade, evaluated in practice of the invention.
Figure 10:
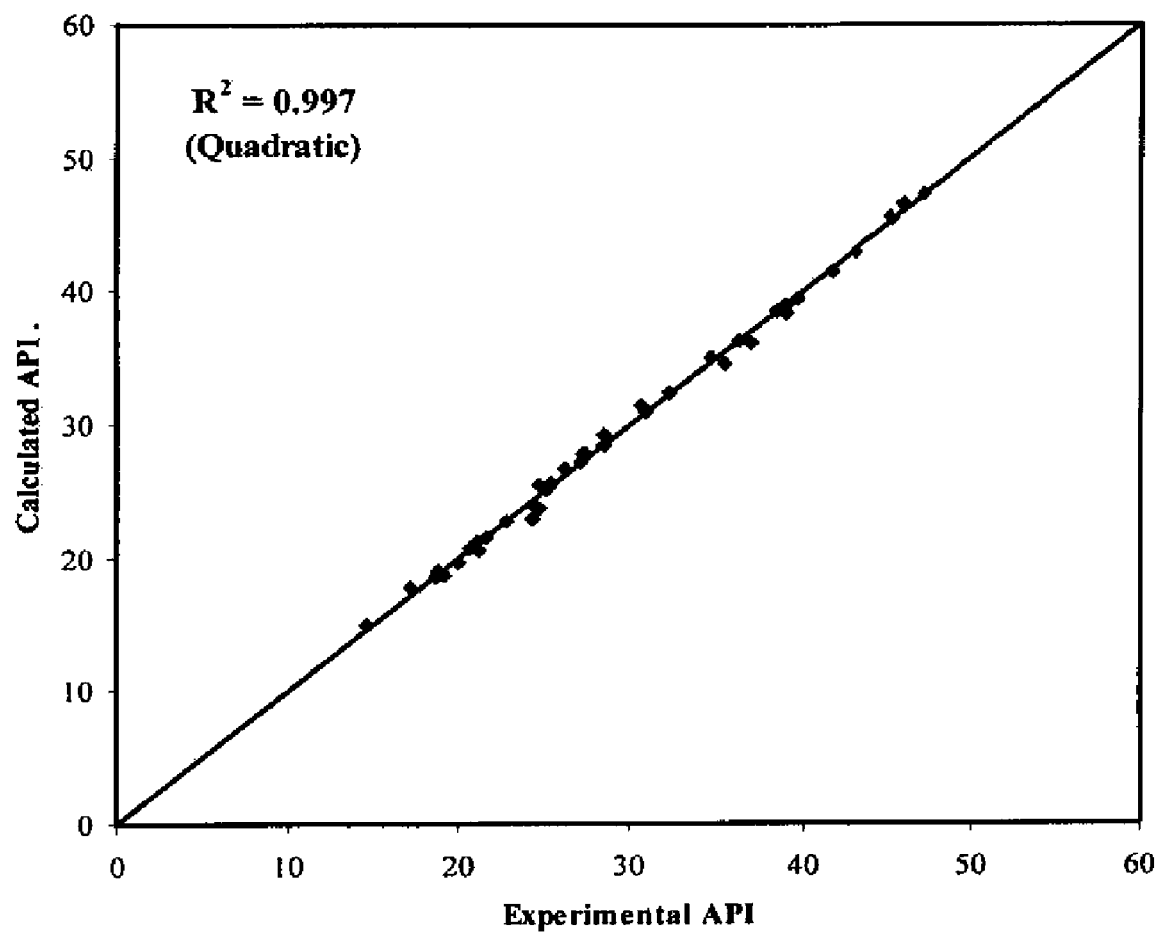
FIG. 10 shows the parity diagram for the API gravity of 42 petroleum factions calculated using quadratic expressions and refractive index measured at 50 to 70 degrees centigrade, evaluated in practice of the invention.

This equation predicts the API gravity with an average error of 1.3% and a correlation coefficient of 0.997 as shown in FIG. 9 and the parity diagram in FIG. 10.

The value of the refractive index outputted from the conventional digital refractometer incorporated (integrated) in this invention is used to calculate the API gravity using the following linear expression.

$$API = -394.12n + 615.12 \quad (9)$$

Figure 11:
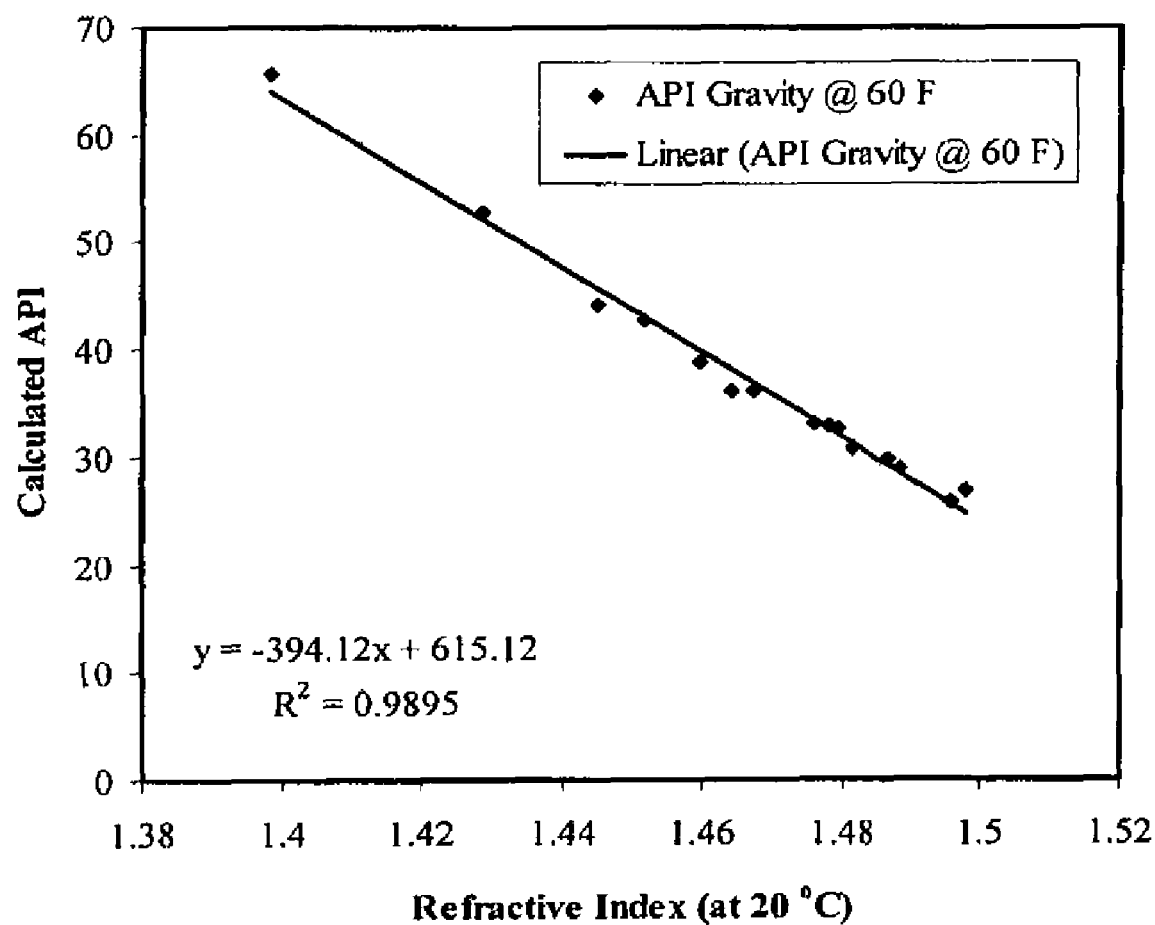
FIG. 11 shows the API gravity of 15 petroleum factions calculated using linear expression and refractive index measured at 20 degrees centigrade, evaluated in practice of the invention.
Figure 12:
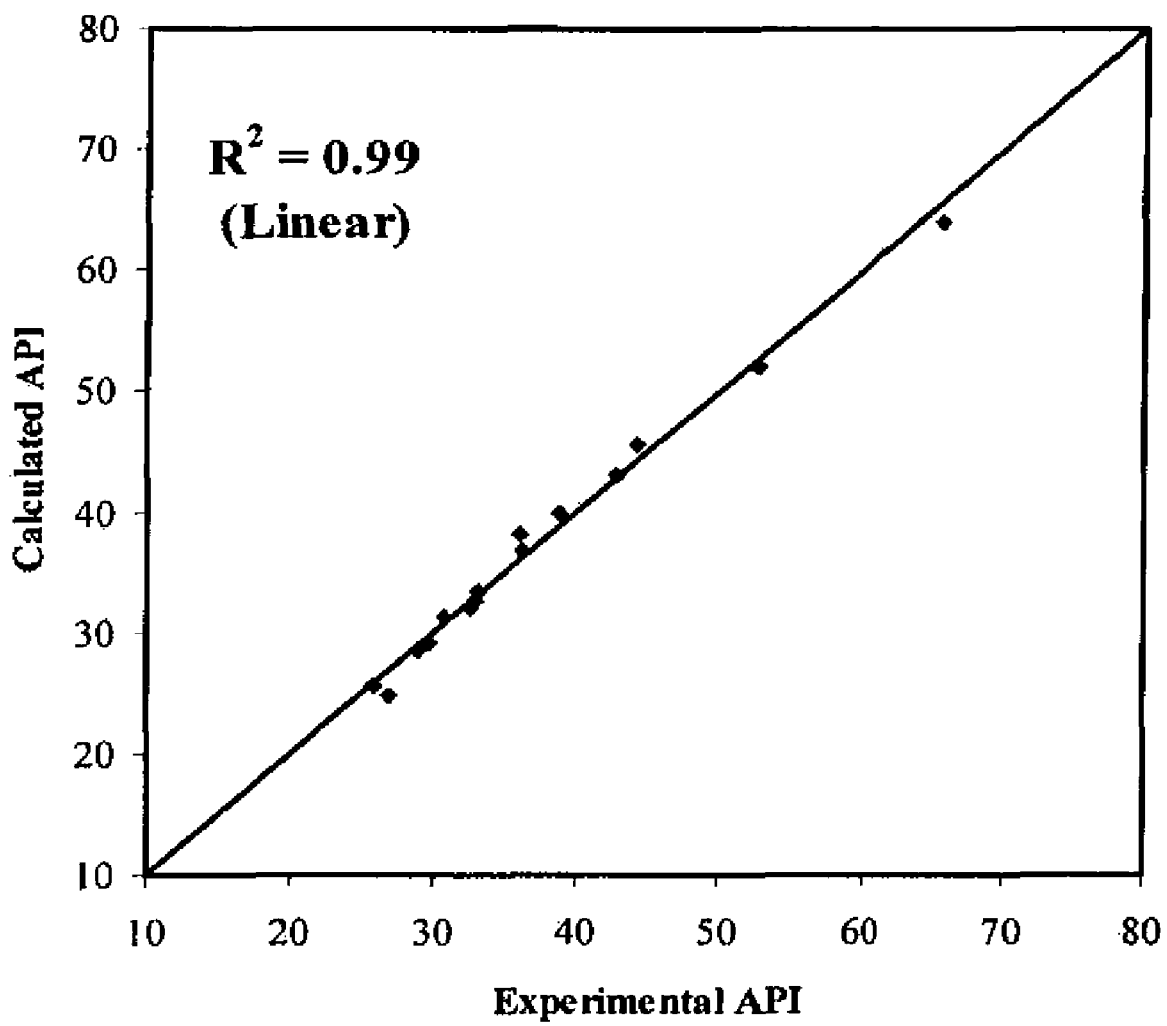
FIG. 12 shows the API gravity of 15 petroleum factions calculated using linear expression and refractive index measured at 20 degrees fro the API gravity of 15 petroleum factions calculated sing linear expression and refractive index measured at 20 degrees centigrade, evaluated in practice of the invention.

This equation was developed using the experimental data for the API gravity of 15 petroleum fractions and refractive index measured at 20 degrees centigrade. This equation applies for petroleum fractions with minimum refractive index of 1.9385 and a maximum of 1.4976 which corresponds to a minimum API of 26 and maximum of 66. The equation is applicable to different types of petroleum fractions like naphta, kerosene, middle distillate, and heavy gasoil. It has an average percentage error of ⅔% and a correlation coefficient of 0.99 as shown in FIG. 11 which is very accurate. The parity diagram showing the accuracy of the predictions is shown in FIG. 12.

Alternatively the following quadratic expression may be used to obtain better predictions $$API = 1.031.6n^2 - 3389.2n + 2788.1 \quad (10)$$

Figure 13:
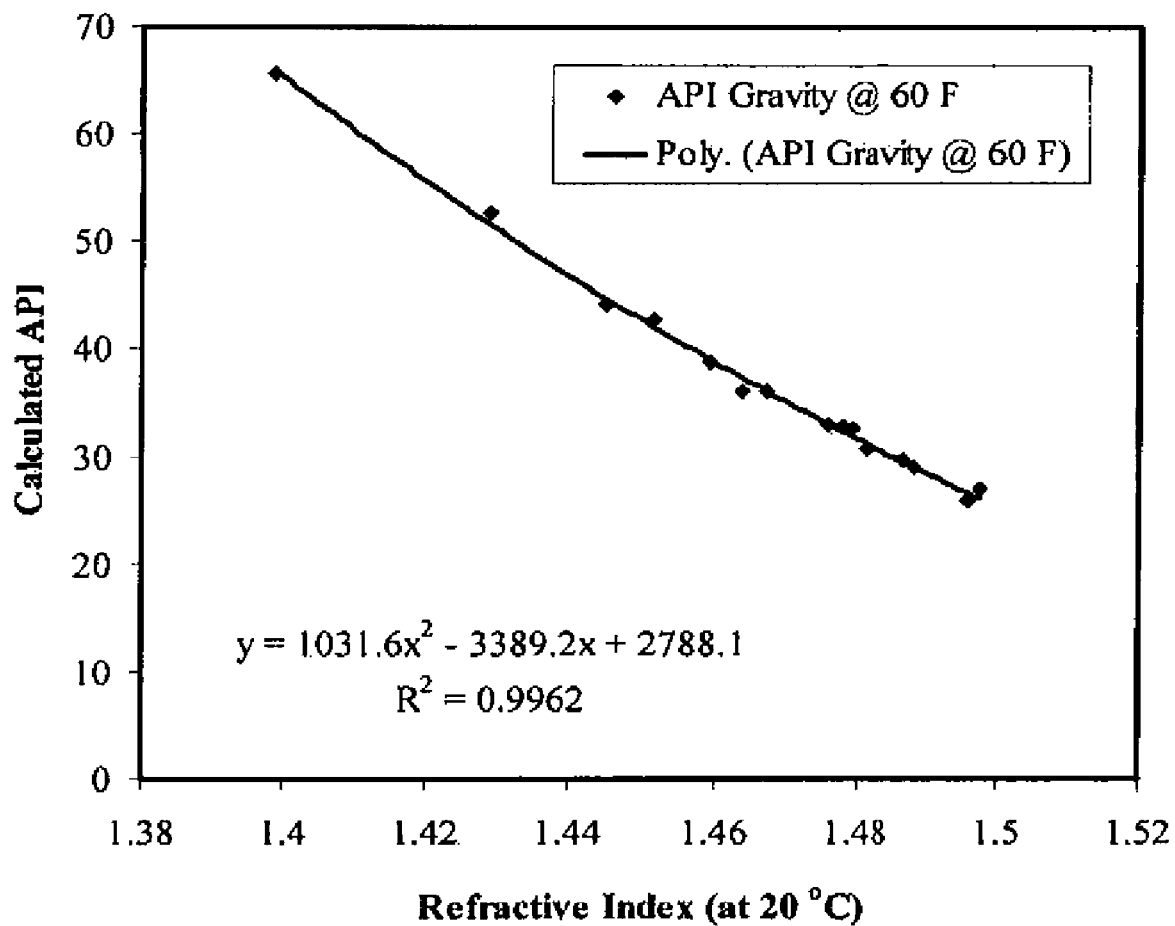
FIG. 13 shows the API gravity of 15 petroleum factions calculated using quadratic expression and refractive index measured at 20 degrees centigrade, evaluated in practice of the invention.
Figure 14:
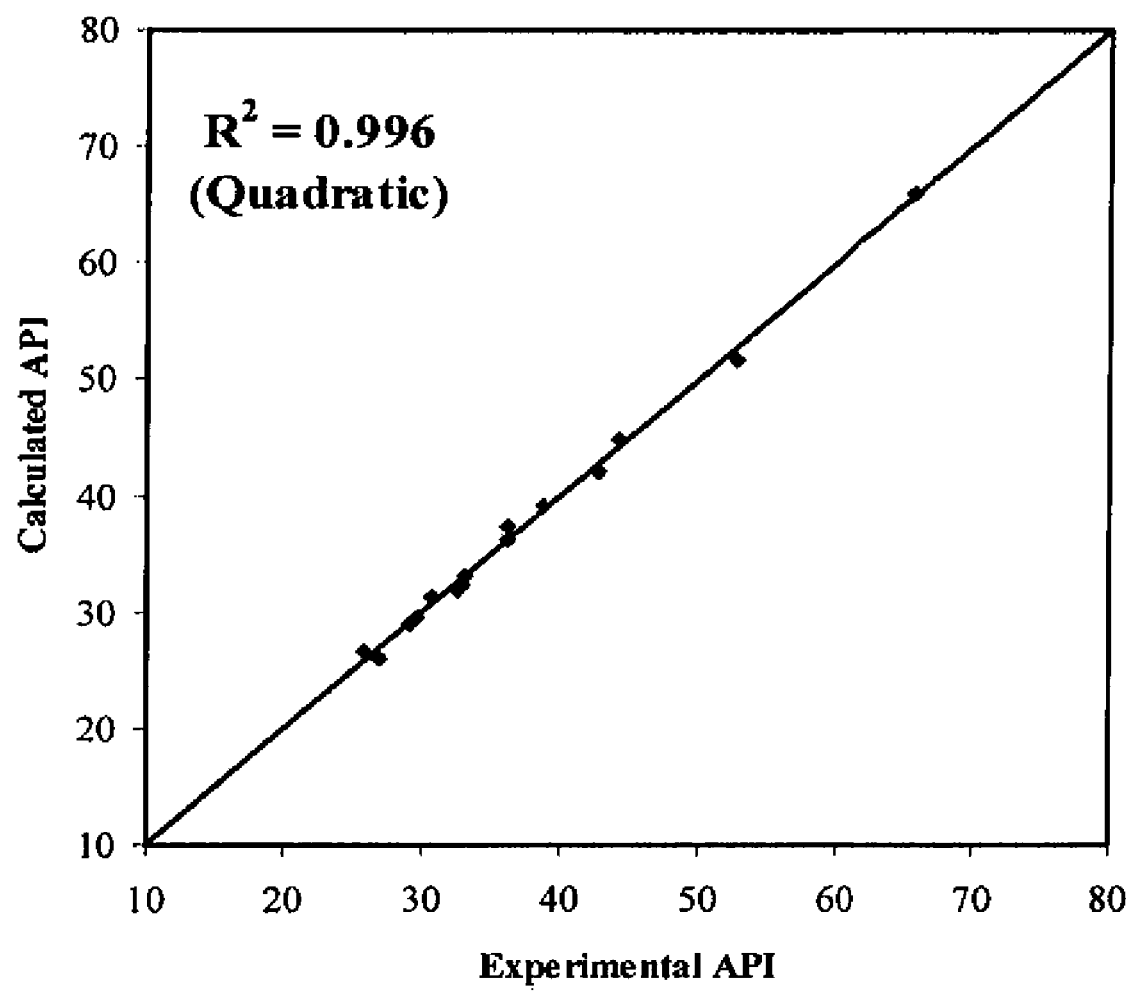
FIG. 14 shows the parity diagram for the API gravity of 15 petroleum fractions calculated using quadratic expression and refractive index measured at 20 degrees centigrade, evaluated in practice of the invention.

This equation predicts the API gravity with an average error of 1.3% and a correlation coefficient of 0.996 as shown in FIG. 13 and the parity diagram in FIG. 14.

The specific gravity SG at 15 degrees centigrade can be obtained from Equation (4) described above.

When at least one additional property is available for a liquid hydrocarbon or petroleum fraction such as the boiling point, molecular weight, critical temperature, critical press, critical volume, heat of vaporization, kinematic viscosity, or density, the correlations present by Riaz (Ind. Eng. Chem. Res., 40, 8, 200, 1976-1984—Chem. Eng. Comm., 176 1999, 1750193) the teachings of which are incorporated herein by reference, may be used to estimate equation of state (EOS) parameters (for such property estimation as density and specific volume in addition to phase behavior and equilibrium calculations), critical constants, the composition of petroleum fractions (in terms of paraffin, thermal conductivity, diffusion coefficient) of hydrocarbon fluids using the refractive index exclusively/alone. Said at least one additional property is estimable by using correlations presented therein from refractive index exclusively which may be obtained by refractometer using a refractometer.

Recently Riazi et. Al. made an extensive analysis of predictive methods and applications of refractive index in prediction of other physical properties of hydrocarbon systems. An evaluation of this method for some petroleum fractions is demonstrated in detail therein. The limitation in these analyses is that an additional parameter is required along with the refractive index rendering the methods presented therein impractical.

To obtain the necessary additional correlating parameter, the calculated API gravity value from the refractive index outputted from the conventional digital refractometer incorporated (integrated) in this invention is used to calculate the petroleum fractions average boiling point using the following exponential expression, $$T_b = (°C.) = 950.09 \exp(-0.0335 API) \quad (11)$$

Where $T_b$ is the ASTM-D86 temperature at 50% volume vaporized in degrees centigrade.

Figure 15:
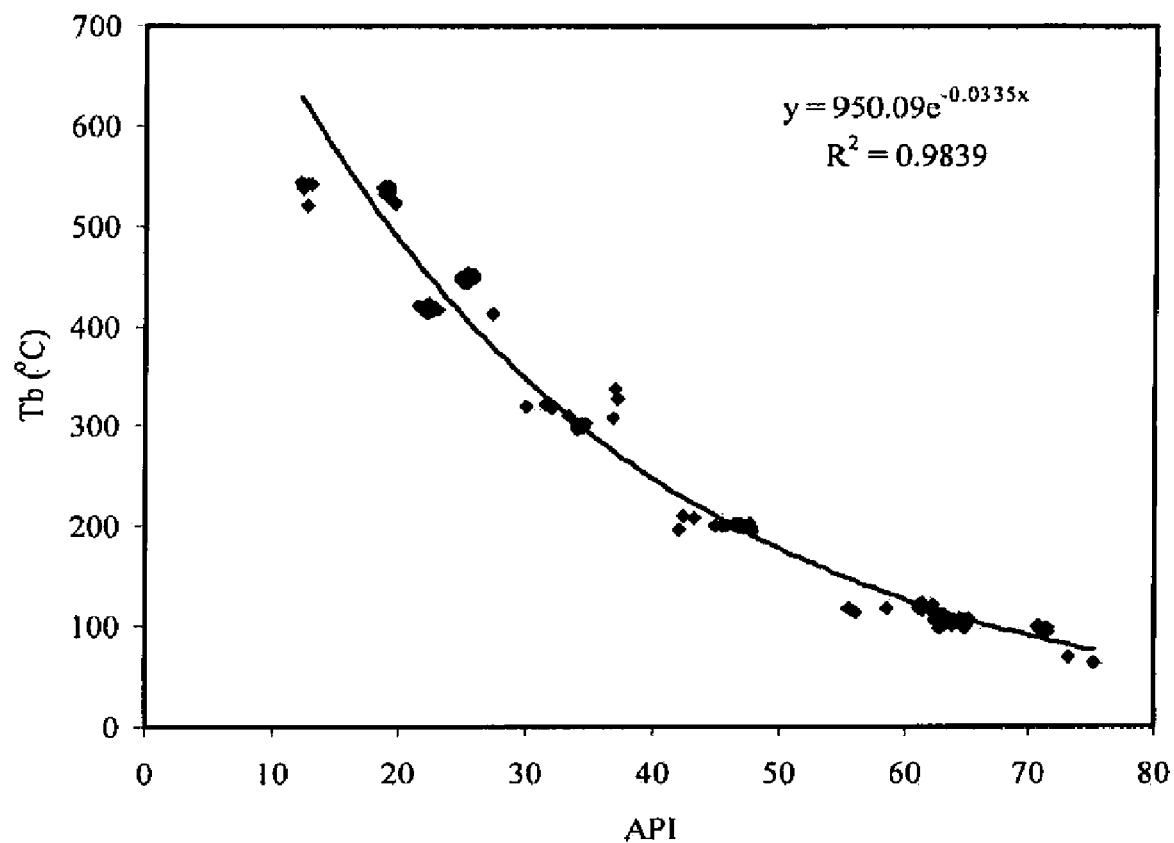
FIG. 15 shows the mid-(average) boiling point of 196 petroleum fraction calculated using exponential expression and API gravity, evaluated in practice of the invention.
Figure 16:
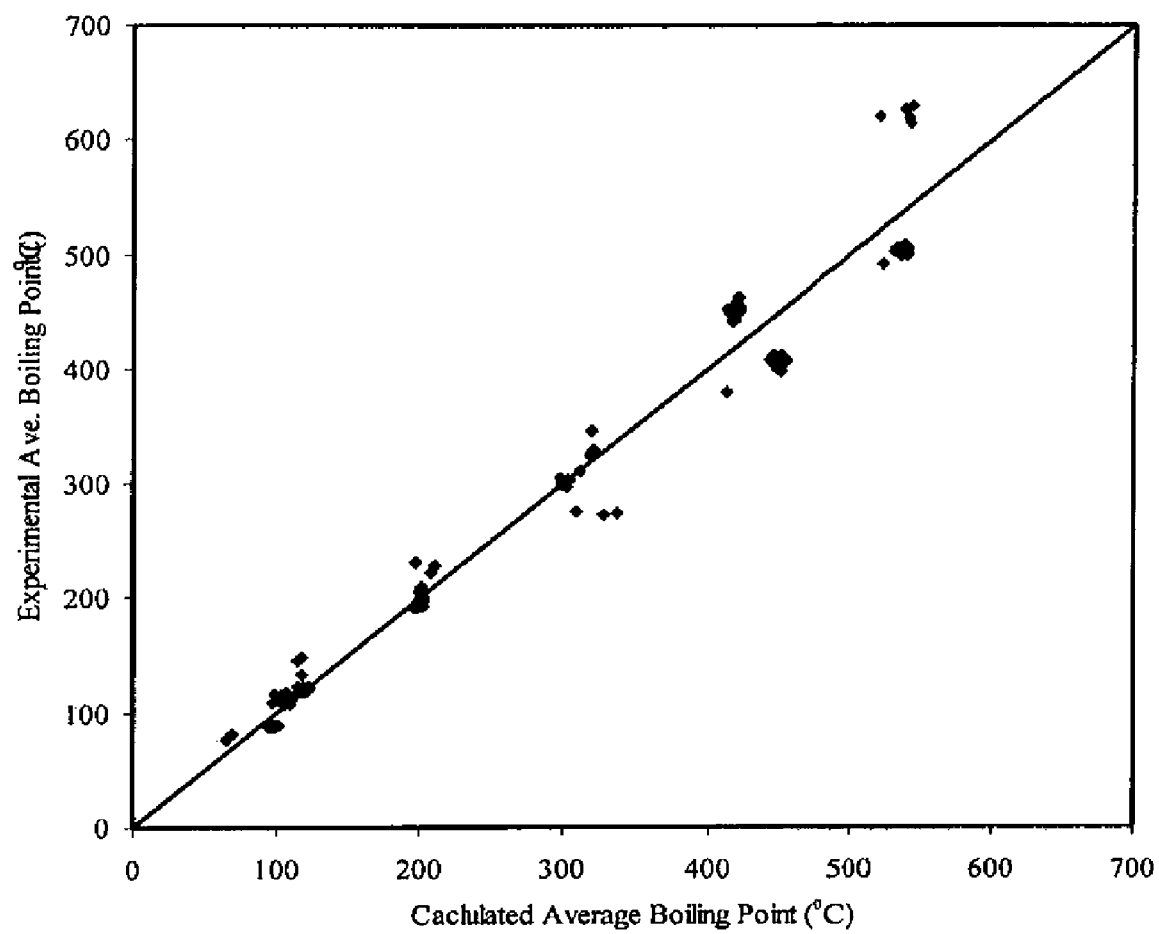
FIG. 16 shows the parity diagram for the Mid-(average) boiling point of 196 petroleum factions calculated using exponential expression and API gravity, evaluated in practice of the invention.

This equation was developed using the experimental data for the average boiling point of 196 petroleum fractions and the API gravity. This equation applies for petroleum fractions with minimum API gravity of 12.3 and a maximum of 75.1 which corresponds to a minimum average boiling point of 64.4 and maximum of 544 degrees centigrade. The equation is applicable to different types of petroleum fractions like light naphtha, saturated naphtha, unsaturated naphtha, heavy naphtha, kerosene, ATK, diesel, gasoil, vacuum gasoil, coker gasoil, atmospheric residue, desulfurized residue. It has an average percentage error of 2.8% (12.6 max.) and a correlation coefficient of 0.98 as shown in FIG. 15 which is very accurate. The parity diagram showing the accuracy of the predictions is shown in FIG. 16.

Figure 2:
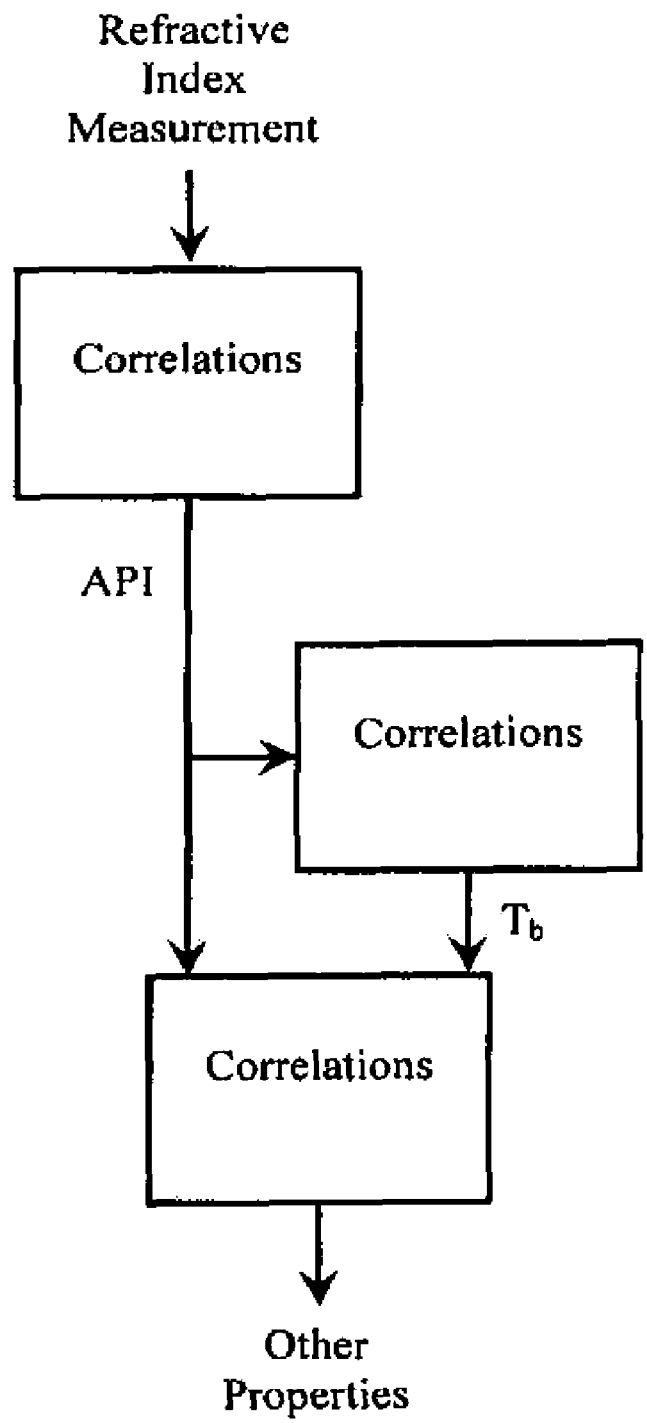
FIG. 2 shows a simplified schematic representation of the model, using the invention within its environment.

Therefore, once the API of the petroleum fraction is determined from RI, it can be used to determine the average (middle) boiling point. Both the refractive index and the average boiling point can e used as in FIG. 2 to calculate more properties using prior art methods described herein and elsewhere.

The most commonly used characterization factor is that proposed by Watson [10]. The Watson or UOP characterization factor which is an index of paraffinicity of the sample requires the mean average boiling point (MeABP) or simply the average boiling point in Kelvin and the standard specific gravity (SG) at 15.6° C. of the petroleum fraction and is defined as follows, $$K_W = \frac{(1.8\,Tb)^{1/3}}{SG} \quad (12)$$

The following relation can be used to determine the critical constants, molecular weight, density, and boiling point, $$\Theta = a_0 \exp(b_0 T_b + c_0 I_{20} + d_0 T_b I_{20}) T_b^{e_0} I_{20}^{f_0} \quad (13)$$

where $\Theta$ is a property such as the critical temperature, $T_c$ (K), critical pressure, $P_c$ (bar), critical volume, $V_c$ (m³/kg), specific gravity at 15.5° C. (60° F.), SG, and the heat of vaporization at the normal boiling point in KJ/Kmol, $\Delta H_v$.

Constants in Equation 13 for various properties: $\Theta = a_0 \exp(b_0 T_b + c_0 I_{20} + d_0 T_b I_{20}) T_b^{e_0} I_{20}^{f_0}$

| $\theta$ | $a_0$ | $b_0$ | $c_0$ | $d_0$ | $e_0$ | $f_0$ | AAD % |
|---|---|---|---|---|---|---|---|
| $T_c$ | $4.4876 \times 10^3$ | $-1.3171 \times 10^{-3}$ | $-16.9097$ | $4.5236 \times 10^{-3}$ | $0.6154$ | $4.3469$ | $0.6$ |
| $P_c$ | $8.4027 \times 10^{23}$ | $-1.2067 \times 10^{-2}$ | $-74.5612$ | $0.0342$ | $-1.0303$ | $18.4330$ | $2.6$ |

| θ | $a_0$ | $b_0$ | $c_0$ | $d_0$ | $e_0$ | $f_0$ | AAD % |
|---|---|---|---|---|---|---|---|
| $V_c$ | $6.712 \times 10^{-6}$ | $-2.72 \times 10^{-3}$ | 0.91548 | $7.92 \times 10^{-3}$ | 0.5775 | -2.1548 | 1.8 |
| MW | $8.9205 \times 10^{-6}$ | $15.5833 \times 10^{-6}$ | 4.2376 | 0 | 2.0935 | -1.9985 | 2.3 |
| SG | $2.4381 \times 10^{7}$ | $-4.194 \times 10^{-4}$ | -23.5535 | $3.9874 \times 10^{-3}$ | -0.3418 | 6.9195 | 0.5 |
| $\Delta H_v$ | 39.741 | 0 | 0 | 0 | 1.13529 | 0.02414 | 1.6 |

The refractive index parameters $I_{20}$, which is considered as a size parameter (defined as the ratio of the actual molar volume of molecules, $R_m$ (molar refraction), to the apparent molar volume of molecules, V), is determined using the following relation from the refractive index n measured experimentally at 20° C., $$I_{20} = \frac{n_{20}^2 - 1}{n_{20}^2 + 2} \quad (14)$$

The density of the petroleum fraction at 20° C. and 1 atm can be determined using one of the following relations depending on the MW of the petroleum fraction, $$\text{For MW} \leq 300 \; d_{20} = 0.9837 T_b^{0.0002} SG^{1.003} \quad (15)$$

$$\text{For MW} > 300 \; d_{20} = 2.8309 MW_b^{0.04} I_{20}^{1.1354} \quad (16)$$

where $T_b$ is in degrees Kelvin.

Alternatively, the molecular weight of light petroleum fractions (where the specific gravity is less than 0.9o7 and the boiling point is less than 840 K) is determined using the API recommended equation [19] which requires only the mean average boiling point ($T_b$) in Kelvin and the standard specific gravity (SG) of the petroleum fraction.

$$MW = 42.965(T_b^{1.26007} SG^{4.98308})[\exp(2.097 \cdot 10^{-4} T_b - 7.78712 SG + 2.08476 \cdot 10^{-3} T_b SG)] \quad (17)$$

The refractivity intercept, Ri and parameter, m are used to characterize the petroleum faction. These parameters are both defined in terms of the sodium D line refractive index at 20° C., $n_{20}$ as follows $$Ri = n_{20} - d_{20}/2 \quad (18)$$

$$M = MW(n_{20} - 1.475) \quad (19)$$

Many properties can be determined using these parameters and these are shown in the work of Riazi among others. The sulfur content and the Paraffin, napthenes, and aromatic content of petroleum fractions are show here just as an example. For fraction with molecular weights of less than 250, the sulfur weight percent (XS) can be calculated with an accuracy of about 0.15 using the following relation:

$$X_s = 177.448 - 170.946 R_i + 0.2258n + 4.054 SG \quad (20)$$

Correlations are also available for heavier petroleum factions with MW more than 250 (Ind. Eng. Chem. Res. 1999, 38, 11, 4507).

For petroleum factions with a MW of less than 250, the volume percent of paraffins, napthenes, and aromatics can be determined using the following correlations with an average error of about 5%, $$X_P = 325.74 - 348.148 + 1.166m \quad (21)$$

$$X_N = -195.71 + 363.853 SG - 3.992m \quad (22)$$

$$X_A = 100 - (XP + XN) \quad (23)$$

Also for petroleum fractions with MW of less than 250, the volume percent of monaromatics, ($X_{MA}$) and polyardomatics (($X_{PA}$) can be determined using the following correlations with an average error of about 5-6%, $$X_{MA} = -6282.45 + 5990.816 Ri - 2.4833m \quad (24)$$

$$X_{PA} = 1188.175 - 1122.13 Ri + 2.3745m \quad (25)$$

Where, $$X_A = X_{MA} + X_{PA} \quad (26)$$

When the calculated value of any of XP, XN, XA is negative then it should be set equal to zero and the other values should be adjusted accordingly, Other correlations are also available for heavier petroleum fractions with MW more than 250 (Ind. Eng. Chem. Res 1986, 25, 4, 1009).

Alternatively, the molecular group-type (paraffins, naphthenes and aromatics) fractional composition for the light petroleum fraction may be determined using the generalized method proposed by Riazi and Daubert. This method determined the mole fractions of the paraffins, $X_P$, napthenes, $X_N$ and aromatics, $X_{Ar}$ using the following equations, $$X_P = -23.94 + 24.21 R_i - 1.092 VGF \quad (27)$$

$$X_N = 41.14 - 39.43 R_i + 0.672 VGF \quad (28)$$

$$X_A = -16.2 + 15.22 R_i + 0.465 VGF \quad (29)$$

$$R_i = n - (d/2) \quad (30)$$

$$n = [(1+2i)/(1-i)]^{0.5} \quad (31)$$

$$VGF = -1.816 + 3.484 SG - 0.1156 v_{37.8} \quad (32)$$

Where $R_i$ is the refractivity intercept, n is the refractive index at 20° C., d ist the density in g/cm³ at 20° C. and 0.1 MPa, VGF is the viscosity gravity function, SG is the specific gravity at 15° C., and is the kinematic viscosity at 38° C. in mm²/s.

The viscosity of petroleum oil at the standard temperatures of 37.58 and 98.9° C. is determined using the following relation by Abbot et. Al.

$$\log v_{37.58} = 4.39371 - 1.94733 K_W + 0.12769 K_W^2 + 3.2629 \times 10^{-4} API^2 - 1.18246 \times 10^{-2} K_W API + \frac{(8.0325 \times 10^{-2} K_W + 1.24899 API + 0.19768 API^2)}{(API + 26.786 - 2.6296 K_W)} \quad (33)$$

$$\log v_{98.9} = -0.463634 - 0.166532 API + 5.13447 \times 10^{-4} API^2 - 8.48995 \times 10^{-3} K_W API + \quad (34)$$

-continued
$$\frac{(8.0325 \times 10^{-2} K_W + 1.24899 API + 0.19768 API^2)}{(API + 26.786 - 2.6296 K_W)}$$

where $K_W$ is Watson's characterization factor, given by Equation (12), API is API gravity given by Equation (3), $v_{37.58}$ is the viscosity at 37.8° C., $v_{98.9}$ is the viscosity at 98.9° C., both in mm²/s, and "log" is the common logarithm.

The liquid thermal conductivity at 25° C. for the petroleum factions is determined using the following correlation, $$\lambda = 2.540312 (SG/T)^{0.5} - 0.0144485 \tag{35}$$

where, $\lambda$ is the thermal conductivity in W/(m,K), T is the temperature in Kelvin equal to 298 K, and SG is the specific gravity.

The Reid vapor pressure (RVP) may be determined using the Riazi-Albahri equation which predicts RVP with an accuracy of 0.06 bar.

$$RVP = P_{cp} \exp(Y) \tag{36}$$

$$Y = -X \left( \frac{T_b SG}{T_t} \right)(1 - T_t)^5$$

$$X = -276.7445 + 0.064447 T_b + 10.0245 SG -$$

$$0.129 T_b SG + \frac{9968.8675}{T_b SG} + 44.6778 \ln T_b + 63.6683 \ln SG$$

$$T_r = 311/T_{cp}$$

where $T_{cp}$ and $P_{cp}$ are the pseudo critical temperature and pressure of the petroleum faction in degrees Kelvin and bar, respectably. SG is the specific gravity at 15.6° C., RVP is in bars and $T_b$ is the normal boiling point in degrees Kelvin.

The pseudo-critical temperature ($T_{cp}$), pseudo-critical pressure ($P_{cp}$) and the accentric factor ($\omega$) of petroleum oil are estimated by the methods of Lee-Kessler as follows, $$T_{cp} = \tag{37}$$
$$189.8 + 450.6 SG + T_b(0.4244 + 0.1174 SG) + \frac{(14{,}410 - 100{,}688 SG)}{T_b}$$

$$\ln P_{cp} = \tag{38}$$
$$5.68925 - \frac{0.0566}{SG} - 10^{-3} T_b \left( 0.436392 + \frac{4.12164}{SG} + \frac{0.213426}{SG^2} \right) +$$
$$10^{-7} T_b^2 \left( 4.75794 + \frac{11.819}{SG} + \frac{1.53015}{SG^2} \right) -$$
$$10^{-10} T_b^3 \left( 2.45055 + \frac{9.901}{SG^2} \right)$$

$$\omega = -7.904 + 0.1352 K_W - \tag{39}$$
$$0.007465 K_W^2 + 8.359 T_{br} + \frac{(1.408 - 0.1063 K_W)}{T_{br}}$$

$$T_{br} = \frac{T_b}{T_c}$$

where $T_{cp}$ is the pseudo critical temperature in Kelvin, $P_{cp}$ pressure in bar, $\omega$ is the acentric factor, $T_b$ is the normal boiling point in Kelvin, SG is the standard specific gravity, $T_{br}$ is the reduced boiling point temperature from Equation (30), $K_W$ is Walton's characterization factor, $T_c$ is the critical temperature in Kelvin, and "In" is the Napierian logarithm.

The isobaric specific heat for a liquid petroleum fraction is estimated by the 1933 correlation attributed to Watson and Nelson.

$$C_{P_l} = 4.185(0.35 + 0.055 K_W) \tag{40}$$
$$(0.3065 - 0.16734 SG + T(1.467 \times 10^{-3} - 5.5088 \times 10^{-4} SG))$$

where $K_W$ is Watson's characterization factor, SG is the standard specific gravity, T is the temperature in Kelvin, and $Cp_1$ is the isobaric mass specific heat for liquid in KJ/kg,K).

The isobaric vapor heat capacity at 15.6° C. is determined using the method of Lee-Kesler also cited in the API technical data book, $$Cp_g = 4.185(B + 3.6CT + 9.72 DT^2) \tag{41}$$

$$B = -0.35644 + 0.02972 K_W + \alpha \left( 0.29502 - \frac{0.2846}{SG} \right)$$

$$C = \frac{-10^{-4}}{2} \left( 2.9247 - 1.5524 K_W + \right.$$
$$\left. 0.05543 K_W^2 + \alpha \left( 6.0283 - \frac{5.0694}{SG} \right) \right)$$

$$D = \frac{-10^{-7}}{3} (1.6946 + 0.0844 \alpha)$$

$\alpha = 0$ unless $10 < K_W < 12.8$ and $0.7 < SG < 0.885$ then $$\alpha = \left[ \left( \frac{12.8}{K_W} - 1 \right) \left( 1 - \frac{10}{K_W} \right) (SG - 0.885)(SG - 0.7) \times 10^4 \right]^2$$

where $C_{pg}$ is the specific heat of petroleum faction in the ideal gas state in KJ/(kg,K), T is the temperature in Kelvin, $K_w$ is Watson's characterization factor, SG is the standard specific gravity, and B, C, and D are coefficients.

The research octane number (RON) is determined by the graphical method of Nelson which we have digitized. The correlation requires the mid-boiling point of gasoline and either the paraffin content or the Watson characterization factor. The mote octane number (MON) is determined from the following correlation derived from that proposed by Jenkins for olefin free fuels,

MON=22.5+0.83RON-20.0SG

Where SG is the specific gravity of the fuel at 15.5° C.

The net heat of combustion is KJ/Kg is approximated by the following API recommended equation as a function of the API gravity and Watson Characterization factor ($K_W$), $$\Delta H_c = 19{,}783.6 + 1969.7 K_v + 267.3 API + 0.2834 API^2 - 23.146 K_w API \tag{43}$$

Another relation that provides equally good results but better correlation is that of Gorenkov et al. for the net heat of combustion of jet fuels in KJ/kg which is modified her for naphtha in the following form, $$\Delta H_c = 35{,}696 + 94.87(X_A) - 9.44(T_{ave}) - 0.35(X_A)(T_{ave}) + \tag{44}$$
$$\frac{5{,}525 - 111.1(X_A) + 10.15(T_{ave}) + 0.377(X_A)(T_{ave})}{0.001 d}$$

where $X_A$ is the content of aromatic hydrocarbons in wt % and $T_{ave}$ is the average boiling point of the fuel ($T_b$) in ° C. and d is the fuel density at 20° C. in kg/m³.

The invention has been explained with reference to some exemplary equation and correlations. It is understood that those skilled in the art will be able to measure the same and other properties, by calculating them using the above parameters, using other equations and correlations which can be done without further experimentations. Those are intended to be encompassed in the claims of this invention.

The above procedure can be applied to measure other properties of the petroleum faction by calculating through various regression techniques from appropriate experimental data the values of the constants of any appropriate equations and correlations. The invention may as well be applied using prior art correlations or digitization of the prior art figures and data tabulations the accuracy of which has already been verified in the prior art references. The refractive index may as well be the true refractive index obtained for refractometer or any refractive index obtainable from a refractive index device, a gas chromatograph, or infrared spectroscopy and the like since these are well established in the prior art or can be easily developed by those skilled in the art without parting from the teachings of the present invention or further experimentation.

When experimental data are available, one could easily correlate the various properties of the petroleum fraction disclosed hereinabove directly with the refractive index using correlations, and algorithms like neural networks, and genetic algorithms for example, or other correlating or data fitting techniques for the purpose of the present invention.

An apparatus comprising such mathematical models is particularly useful of recognizing and identifying organic compounds such as complex hydrocarbons, whose properties conventionally require a high level of training and may hours of hard work to identify, and are frequently indistinguishable from one another by human interpretation. The method and apparatus of the present invention is useful for the measuring the properties of pure hydrocarbon liquids and petroleum fractions in the laboratory or (on-site) easily and rapidly in one single test from a small sample with accurate results using a simple inexpensive refractometer. It is also useful for property measurements in the field in automatic inline analyzers for quality assurance and in advanced control strategy systems to control production operations to meet required product specifications. The said invention provides increased speed of fingerprinting analysis, accuracy and reliability together with a decrease learning curve and heightened objectivity for the analysis.

Property measurement of petroleum fractions using neural networks

An artificial intelligence system can be used with refractive index data to provide a method of improving recognition of an unknown from its boiling pattern by training the neural networks from appropriate experimental data. Customized neural network systems allow the ultimate organization and resourceful use of variables already existing in the refractive index apparatus (refractometer) for a much more comprehensive, discrete, and accurate differentiation and matching of boiling point than is possible with human memory.

Detail description of the neural network architecture that can be used for the purpose of this invention is explained in details in Albari the teaching of which are incorporated herein by reference. Those experts in the art can easily ascertain that any network type, network architecture, input range, training function, adaptive learning function, and transfer function may be used without departing from the spirit and scope of the present invention and are all claimed herein.

Preferred Embodiments

Figure 17:
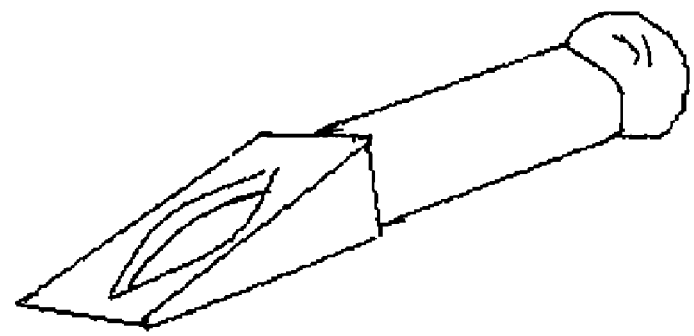
FIG. 17 shows a handheld analyzer, a Laboratory benchtop analyzer and an inline process sample analyzer.
Figure 17:
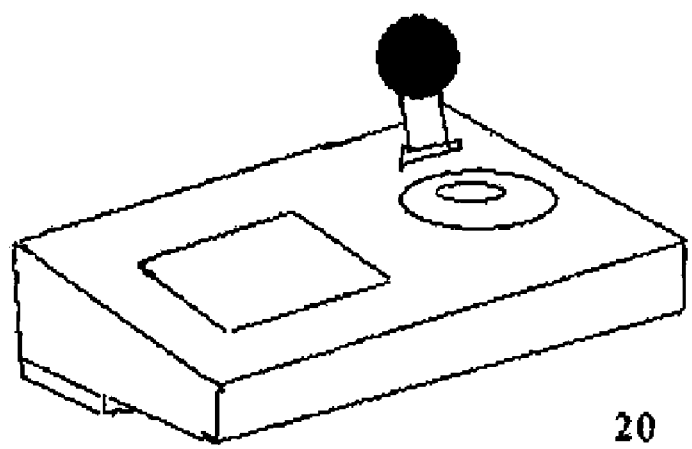
Figure 17:
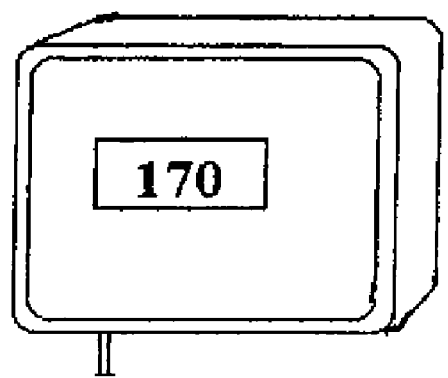

The above and other aspects, features, and advantages of the present invention will be better and more fully understood by reference to the following detailed and more particular description of the invention, present in conjunction with the following examples which are provided to further define the invention and are in non way meant to limit the scope of the invention to the particulars of these examples, wherein:

FIG. 17 shows a handheld analyzer 10, a Laboratory bench-top analyzer 20 and an inline process sample analyzer 30.

The Invention Handheld or Laboratory Bench-Top Digital Analyzer

Figure 3:
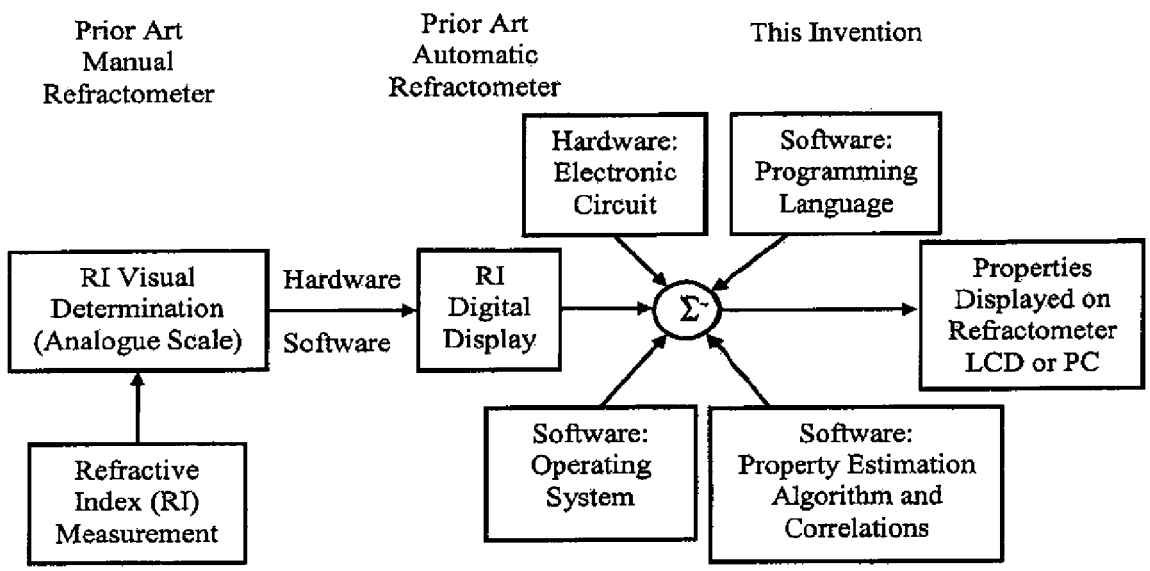
FIG. 3 shows a simplified block diagram of the components of the apparatus for the invention within its environment.

In a preferred embodiment with refereeing to the accompanying figures, and in particular to FIG. 3, the present invention uses the prior digital refractive index analyzer (refractometer) which measures and digitally displays the refractive index then using electronic circuit and software comprising operating system, programming language, property estimation algorithms and correlations to calculate the various thermophysical properties of a hydrocarbon sample from its refractive index property then output (display) said properties instead of (or along with) displaying the refractive index number.

The present invention may be used as a handheld 10 or laboratory bench-top digital analyzer 20 wherein a small sample of the product analyzed using refractomentry and outputting the measured property value to be displayed on an LCD screen on the analyzer apparatus or on the screen of a computer 40 interfaced with the analyzer apparatus.

As Inline Digital Analyzer

The present invention may be used as an inline analyzer 30 wherein an automatic system is used to automatically draw a small sample of the product, analyze it using refractometry, then disposing it and outputting the measured property value to the advanced control strategy system or displaying it in the control room to the operator for action.

A non-limiting example would be to control the crude oil distillation units main fractionator overhead temperature using output from such inline analyzer placed on the naphtha product to provide set-point to the fractionator overhead temperature controller to increase overhead temperature when naphtha API is measured by an inline analyzer and found to be lower than required specifications.

Another non-limiting example would be to control the crude oil distillation unit main fractionator diesel product API using output from such inline analyzer 30 for the diesel product, to provide set-point to diesel draw-off rate controller from the fractionator to increase the diesels draw-off rate when measured API by such inline analyzer 30 is found to be lower than required specifications.

EQUIVALENTS

From the foregoing description, one skilled in the art can easily ascertain the essential characteristics of this invention and, without departing from the spirit and scope thereof, can make various changes and modifications of the invention to adapt it to various usages and conditions.

Such variations and changes may include, but are not limited to, using other mathematical or computational methods such as suing other generalized correlations, neural networks algorithms, genetic algorithms, or an other correlation method that can still represent the chemical and physical behavior of the petroleum fraction. It is believed that such can be accomplished without excessive experimentation. In any case, any such variations are all claimed under the scope of this invention.

Those experts in the art will also realize that the method of invention as explained by exemplary equations, correlations, and conditions and is not to be construed as limiting but only to provide examples.

The methods of the present invention have been explained with reference to plurality of references the teachings of which are all incorporated herein by reference.

This invention has been described hereinabove, although with reference to a plurality of illustrative exemplary and preferred embodiments, it is to be understood that it is in no way to be construed as limiting. However, it is readily appreciated that, from reading this disclosure, the invention my be embodied in other specific forms without departing from the spirit or essential characteristics or attributes to bring modifications by replacing some elements for this invention as practiced by their equivalents, which would achieve the same goal and thereof and accordingly reference should be made to the appended claims, rather than to the foregoing specification, as indicating the scope of the invention. Accordingly, those skilled in the art will recognize, or be able to ascertain using no more than routine experimentation, many equivalents to the specific embodiments and the scope of the invention being indicated by the appended claims described herein. Such equivalents, obvious variations, and all changes which come within the meaning and equivalency of the claims are therefore intended to be encompassed therein and are deemed covered by the claims of this invention.

From the foregoing description, one skilled in the art can easily ascertain the essential characteristics of this invention and, without departing from the spirit and scope thereof, can make various changes and modifications of the invention to adapt it to various usages and conditions. Such variations and changes may include, for example, altering the number of components in the housing or using equivalents. It is believed that such can be accomplished without excessive experimentation. In any case, any such variations are all claimed under the scope of this invention.

| Nomenclature | |
|---|---|
| $\lambda =$ | Liquid thermal conductivity @ 25° C. |
| $\Omega =$ | Paraffin, Naphthene, or Aromatic content. |
| $(\Delta H_v)_{Tb} =$ | Heat of vaporization @ NBP. |
| $\sigma_{25} =$ | Surface tension for liquid @ 25° C. |
| $\Delta H_c =$ | Net heat of combustion @ 25° C. |
| $\Phi i =$ | Surface fraction. |
| $Cp_g =$ | Specific heat of petroleum fraction 15.6° C. in the ideal gas state. |
| $Cp_l =$ | Isobaric mass specific heat for liquid 15.6° C. |
| $d =$ | Density in g/cm³ at 20° C. and 0.1 MPa. |
| $H_2 =$ | Hydrogen content. |
| $K =$ | Liquid thermal conductivity at 25° C. |
| $K_w =$ | Watson characterization factor. |
| $P_c =$ | Critical pressure. |
| $Pc_p =$ | Pseudo-critical pressure. |
| $P^v_{37.8} =$ | Vapor pressure at 37.8° C. |
| $n =$ | Refractive index at 20° C. |
| $R_i =$ | Refractivity intercept. |
| $Ta =$ | Aniline point. |
| $T_b =$ | Normal boiling point at 1 atm. |
| $T_{br} =$ | Reduced boiling point temperature. |
| $T_c =$ | Critical temperature. |
| $Tc_m =$ | True critical temperature of the mixture. |
| $Tc_p =$ | Pseudo-critical temperature. |
| $T_f =$ | Freezing temperature. |
| $T_r =$ | Reduced temperature. |
| $VGF =$ | Viscosity gravity function. |
| $X_A =$ | Mole fraction of aromatics. |
| $X_N =$ | Mole fraction of naphthenes. |
| $X_p =$ | Mole fractions of paraffins. |
| $Zc =$ | Critical compressibility factor. |
| $v_{37.8} =$ | Viscosity at 37.8° C. |
| $v_{98.9} =$ | Viscosity at 98.9° C. |
| $v_{38} =$ | Kinematic viscosity at 38° C. in mm²/s. |
| $\omega =$ | Acentric factor. |

-continued

| Nomenclature | |
|---|---|
| API = | API gravity. |
| FBP = | Final boiling point. |
| IBP = | Initial boiling point. |
| MW = | molecular weight. |
| NBP = | Normal boiling point. |
| PNA = | Paraffins, Naphthenes, and Aromatics. |
| $P_t =$ | True vapor pressure of petroleum fraction. |
| RVP = | Reid vapor pressure. |
| SG = | Standard specific gravity for liquid at 15.6° C. |
| TVP = | True vapor pressure. |

I claim as my invention is:

1. A method of measuring petroleum fractions, comprising the steps of:
   a) measuring a refractive index n of a petroleum fluid using refractometry;
   b) measuring a kinematic viscosity v of the petroleum fluid;
   c) calculating an API gravity of the petroleum fluid as API=−320.77n+501.4 if n is between 1.42 and 1.5227, and calculating the API gravity as API=−394.12n+615.12 if n is between 1.9385 and 1.4976;
   d) calculating a specific gravity SG of the petroleum fluid as

SG=141.5/(API+131.5);

e) calculating a density d of the petroleum fluid;
   f) calculating a viscosity gravity function VGF of the petroleum fluid as VGF=−1.816+3.484SG−0.1156v;

g) calculating a refractivity intercept Ri as Ri=n−d/2;
   h) calculating a mole fraction of paraffins as Xp=−23.94+24.21Ri−1.092VGF;
   i) calculating a mole fraction of naphthenes as Xn=41.14−39.43Ri+0.672VGF; and
   j) calculating a mole fraction of aromatics as Xa=−16.2+15.22Ri+0.465VGF.

2. The method of measuring petroleum fractions as recited in claim 1, wherein the kinematic viscosity of the pure hydrocarbon fluid is measured at a temperature of 38° C.

3. The method of measuring petroleum fractions as recited in claim 2, further comprising the step of calculating a petroleum fractions average boiling point $T_b$ as $T_b=950.09e^{-0.0335 API}$.

4. The method of measuring petroleum fractions as recited in claim 3, further comprising the step of calculating an index of paraffinicity $K_W$ as $$K_W = \frac{(1.8T_b)^{1/3}}{SG}.$$

5. The method of measuring petroleum fractions as recited in claim 4, further comprising the step of calculating molecular weight MW as MW=$8.9205 \times 10^{-6} e^{15.5833 \times 10^{-6} T_b + 4.2376} T_b^{2.0935} I^{-1.9985}$, where I a refractive index parameter, given by $$I = \frac{n^2-1}{n^2+2}.$$

6. The method of measuring petroleum fractions as recited in claim 5, wherein said step of calculating the density comprises calculating the density d as $d=0.9837T_b^{0.002}SG^{1.005}$ if MW is less than or equal to 300, calculating the density d as $d=2.8309MW^{0.04}I^{1.1354}$ if MW is greater than 300.

7. A method of measuring petroleum fractions, comprising the steps of:
  a) measuring a refractive index n of a petroleum fluid using refractometry;
  b) measuring a kinematic viscosity v of the petroleum fluid;
  c) calculating an API gravity of the petroleum fluid as $API=1031.6n^2-3389.2n+2788.1$;
  d) calculating a specific gravity SG of the petroleum fluid as $SG=141.5/(API+131.5)$;

e) calculating a density d of the petroleum fluid;
  f) calculating a viscosity gravity function VGF of the petroleum fluid as $VGF=-1.816+3.484SG-0.1156v$;

g) calculating a refractivity intercept Ri as $Ri=n-d/2$;
  h) calculating a mole fraction of paraffins as $Xp=-23.94+24.21Ri-1.092VGF$;
  i) calculating a mole fraction of naphthenes as $Xn=41.14-39.43Ri+0.672VGF$; and
  j) calculating a mole fraction of aromatics as $Xa=-16.2+15.22Ri+0.465VGF$.

8. The method of measuring petroleum fractions as recited in claim 7, wherein the kinematic viscosity of the pure hydrocarbon fluid is measured at a temperature of 38° C.

9. The method of measuring petroleum fractions as recited in claim 8, further comprising the step of calculating a petroleum fractions average boiling point $T_b$ as $T_b=950.09e^{-0.0335API}$.

10. The method of measuring petroleum fractions as recited in claim 9, further comprising the step of calculating an index of paraffinicity $K_W$ as $$K_W = \frac{(1.8T_b)^{1/3}}{SG}.$$

11. The method of measuring petroleum fractions as recited in claim 10, further comprising the step of calculating molecular weight MW as $MW=8.9205\times10^{-6}e^{15.5833\times10^{-6}T_b+4.2376}T_b^{2.0935}I^{-1.9985}$, where I is a refractive index parameter, given by $$I = \frac{n^2-1}{n^2+2}.$$

12. The method of measuring petroleum fractions as recited in claim 11, wherein said step of calculating the density comprises calculating the density d as $d=0.9837T_b^{0.002}SG^{1.005}$ if MW is less than or equal to 300, calculating the density d as $d=2.8309MW^{0.04}I^{1.1354}$ if MW is greater than 300.

13. A method of measuring hydrocarbon fractions, comprising the steps of:
  a) measuring a refractive index n of a pure hydrocarbon fluid using refractometry;
  b) measuring a kinematic viscosity v of the pure hydrocarbon fluid;
  c) calculating an API gravity of the pure hydrocarbon fluid as $API=5\times107e^{-9.5788n}$;

d) calculating a specific gravity SG of the pure hydrocarbon fluid as $SG=141.5/(API+131.5)$;

e) calculating a density d of the pure hydrocarbon fluid as $d=SG-4.5\times10^{-3}(2.34-1.9SG)$;

f) calculating a viscosity gravity function VGF of the pure hydrocarbon fluid as $VGF=-1.816+3.484SG-0.1156v$;

g) calculating a refractivity intercept Ri as $Ri=n-d/2$;
  h) calculating a mole fraction of paraffins as $Xp=-23.94+24.21Ri-1.092VGF$;
  i) calculating a mole fraction of naphthenes as $Xn=41.14-39.43Ri+0.672VGF$; and
  j) calculating a mole fraction of aromatics as $Xa=-16.2+15.22Ri+0.465VGF$.

14. The method of measuring hydrocarbon fractions as recited in claim 13, wherein the kinematic viscosity of the pure hydrocarbon fluid is measured at a temperature of 38° C.

* * * * *